US008574834B2

(12) United States Patent
Kouznetsov et al.

(10) Patent No.: US 8,574,834 B2
(45) Date of Patent: Nov. 5, 2013

(54) METHOD FOR PREDICTING THE RESPONSE TO A THERAPY

(75) Inventors: Nikolai Kouznetsov, Jarfalla (SE); Lisa Charlotta Bandholtz, Stockholm (SE); Alexander Gielen, Bandhagen (SE); Oliver Von Stein, Upplands Vasby (SE); Petra Von Stein, Upplands Vasby (SE)

(73) Assignee: Index Pharmaceuticals AB, Stockholm (SE)

( * ) Notice: Subject to any disclaimer, the term of this patent is extended or adjusted under 35 U.S.C. 154(b) by 378 days.

(21) Appl. No.: 12/746,758

(22) PCT Filed: Dec. 12, 2008

(86) PCT No.: PCT/SE2008/051446
§ 371 (c)(1),
(2), (4) Date: Jul. 22, 2010

(87) PCT Pub. No.: WO2009/078793
PCT Pub. Date: Jun. 25, 2009

(65) Prior Publication Data
US 2010/0285477 A1 Nov. 11, 2010

(30) Foreign Application Priority Data
Dec. 14, 2007 (SE) ...................................... 0702789

(51) Int. Cl.
*C12Q 1/68* (2006.01)
(52) U.S. Cl.
USPC .......................................... 435/6.1; 435/6.11
(58) Field of Classification Search
None
See application file for complete search history.

(56) References Cited

U.S. PATENT DOCUMENTS

| 2004/1019778 | 10/2004 | Sugita et al. |
| 2006/0046259 A1 | 3/2006 | Baird et al. |
| 2007/0248978 A1 | 10/2007 | Lal et al. |

FOREIGN PATENT DOCUMENTS

| WO | WO 03/021261 A2 | 3/2003 |
| WO | WO 03/062792 A2 | 7/2003 |
| WO | WO 2007/004977 A1 | 1/2007 |
| WO | WO 2007/050034 A1 | 5/2007 |

OTHER PUBLICATIONS

Strausberg et al, In Microarrays and Cancer Research, 2002, Warrington et al (eds.), Eaton Publishing, Westborough, MA, pp. xi-xvi.*
Notterman et al, In Microarrays and Cancer Research, 2002, Warrington et al (eds.), Eaton Publishing, Westborough, MA, pp. 81-111.*

Donn et al., "Use of gene expression profiling to identify a novel glucocorticoid sensitivity determining gene, BMPRII", *FASEB J.*, (2):402-14 (2007). Epub Dec. 21, 2006.
Högger et al., "Identification of the integral membrane protein RM3/1 on human monocytes as a glucocorticoid-inducible member of the scavenger receptor cysteine-rich family (CD163)", *J. Immunol.*, 161(4):1883-90 (1998).
Myoumoto et al., "Glucocorticoid-induced granzyme A expression can be used as a marker of glucocorticoid sensitivity for acute lymphoblastic leukemia therapy", *J. Hum. Genet.*, 52(4):328-333 (2007). Epub Feb. 20, 2007.
Woodruff et al., "Genome-wide profiling identifies epithelial cell genes associated with asthma and with treatment response to corticosteroids", *Proc. Natl. Acad. Sci. USA.*, 104(40):15858-63 (2007). Epub Sep. 26, 2007.
Galon et al., "Gene Profiling Reveals Unknown Enhancing and Suppressive Actions of Glucocorticoids on Immune Cells," *FASEB J.* (2002), 16:61-71.
Vermeer et al., "An in vitro Bioassay to Determine Individual Sensitivity to Glucocorticoids: Induction of FKBP51 mRNA in Peripheral Blood Mononuclear Cells," *Mol. Cell. Endocrinol.* (2004), 218:49-55, Elsevier Ireland Ltd.
Wu et al., "Microarray Analysis Reveals Glucocorticoid-Regulated Survival Genes that are Associated with Inhibition of Apoptosis in Breast Epithelial Cells," *Cancer Res.* 64:1757-1764.
Adani et al., "The Role of Cytomegalovirus in Inflammatory Bowel Disease and Gastrointestinal Lymphoma", *Gastroenterology* 123:390-395, 2002.
Buechler et al., "Regulation of scavenger receptor CD163 expression in human monocytes and macrophages by pro- and anti-inflammatory stimuli", *J. Leukocyte Biology*, 67:97-103, 2000.
Gomollon et al., Chrohnology: A tale of time and times and inflammatory bowel diseases, *World J. Gastroenterol* 14(36):5489-5490, 2008.
Iho et al., Oligodeoxynucleotides Containing Palindrome Sequences with Internal 5'-CpG-3' Act Cirectly on Human NK and Activated T Cells to Induce IFN-{gamma} Production in Vitro, *J. Immunol.* 163:3642-3652, 1999.
Jakob et al., "Activation of Cutaneous Dendritic Cells by CpG-Containing Oligodeoxynucleotides: A Role for Dendritic Cells in the Augmentation of Th1 Responses by Immunostimulatory DNA", *J. Immunology* 161:3042-3049, 1998.

(Continued)

*Primary Examiner* — James Martinell
(74) *Attorney, Agent, or Firm* — Porter Wright Morris & Arthur LLP

(57) ABSTRACT

The invention concerns an in vitro method for selecting the therapy for a steroid resistant patient, wherein the method comprises isolating cells from a sample taken from said patient; cultivating said isolated cells in the presence of a steroid, an immunomodulatory oligonucleotide or a mixture thereof; determining an expression level of at least one marker gene in said isolated cells; and comparing said expression level of said at least one marker gene to a value obtained from the cultivation of cells from a healthy person in the presence of a steroid, an immunomodulatory oligonucleotide or a mixture thereof, or to a normalized value obtained from a healthy population. Examples of marker genes are CD163, Tsp1, IL1-R2, TLR2, TLR4, MKP-1 and TXK.

15 Claims, 10 Drawing Sheets

(56) References Cited

OTHER PUBLICATIONS

Kreig, "Lymphocyte activation by CpG dinucleotide motifs in prokaryotic DNA", *Trends in Microbiology* 73(4) No. 2, 1996.

Leung et al., "Steroid-Unresponsive Asthma", *Seminars in Respiratory and Critical Care Medicine* vol. 23, No. 4, 2002.

Leung et al., "Steroid Resistant Asthma", *National Jewish Medical and Research Center*, 2007.

Mannon et al., "Anti-Interleukin-12 Antibody for Active Crohn's Disease", *N. Engl J. Med* 351:2069-2079, 2004.

Mariette, "Anti-cytokines dans le traitement de l'inflammation", *La Revue Du Praticien* 53:507-511, 2003.

Munck, "Physiological Functions of Glucocorticoids in Stress and Their Relation to Pharmacological Actions", *Endocrine Reviews* 5(1):25-44, 1984.

Munkholm et al., "Frequency of glucocorticoid resistance and dependency in Crohn's disease", *Gut* 35:360-362, 1994.

Neurath et al., "Antibodies to Interleukin 12 Abrogate Established Experimental Colitis in Mice", *J. Experimental Medicine* 182:1281-1290, 1995.

Re et al., "The Type II 'Receptor' As a Decoy Target for Interleukin 1 in Polymorphonuclear Leukocytes: Characterization of Induction by Dexamethasone and Ligand Binding Properties of the Released Decoy Receptor", *J. Exp. Med* 179:739-743, 1994.

Stacey et al., "Macrophages Ingest and Are Activated by Bacterial DNA'", *J. Immunology* 157:2116-2122, 1996.

Takeba et al., "Txk, a Member of Nonreceptor Tyrosine Kinase of Tec Family, Acts as a Th1 Cell-Specific Transcription Factor and Regulates IFN-{gamma} Gene Transcription", *J. Immunol.* 168:2365-2370, 2002.

Wohlleben et al., "Immune Stimulatory Strategies for the Prevention and Treatment of Asthma", *Current Pharmaceutical Design* 12:3281-3292, 2006.

Zhao et al., "Effect of Different Chemically Modified Oligodeoxynucleotides on Immune Stimulation", *Biochemical Pharmacology* 51:173-182, 1996.

Zimmermann et al., "Cutting Edge: CpG Oligodeoxynucleotides Trigger Protective and Curative Th1 Responses in Lethal Murine Leishmaniases", *J. Immunol.* 160:3627-3630, 1998.

Kline, "Effects of CpG DNA on Th1/Th2 balance in asthma", Curr. Top. Microbiol. Immunol., 247:211-225 (2000).

* cited by examiner

SEQUENCE LISTING

```
<160> NUMBER OF SEQ ID NOS: 14

<210> SEQ ID NO 1
<211> LENGTH: 23
<212> TYPE: DNA
<213> ORGANISM: Artificial
<220> FEATURE:
<223> OTHER INFORMATION: PCR primer

<400> SEQUENCE: 1
gctgcagtga attgcacaga tat                                          23

<210> SEQ ID NO 2
<211> LENGTH: 18
<212> TYPE: DNA
<213> ORGANISM: Artificial
<220> FEATURE:
<223> OTHER INFORMATION: PCR primer

<400> SEQUENCE: 2
cgggatgagc gacctgtt                                                18

<210> SEQ ID NO 3
<211> LENGTH: 22
<212> TYPE: DNA
<213> ORGANISM: Artificial
<220> FEATURE:
<223> OTHER INFORMATION: PCR primer

<400> SEQUENCE: 3
```

```
catccgcaaa gtgactgaag ag                                              22

<210> SEQ ID NO 4
<211> LENGTH: 27
<212> TYPE: DNA
<213> ORGANISM: Artificial
<220> FEATURE:
<223> OTHER INFORMATION: PCR primer

<400> SEQUENCE: 4
gtactgaact ccgttgtgat agcatag                                         27

<210> SEQ ID NO 5
<211> LENGTH: 26
<212> TYPE: DNA
<213> ORGANISM: Artificial
<220> FEATURE:
<223> OTHER INFORMATION: PCR primer

<400> SEQUENCE: 5
tcactaggag tattgagcta cgcatc                                          26

<210> SEQ ID NO 6
<211> LENGTH: 23
<212> TYPE: DNA
<213> ORGANISM: Artificial
<220> FEATURE:
<223> OTHER INFORMATION: PCR primer

<400> SEQUENCE: 6
attgtcagtc ttgacccccag aga                                            23

<210> SEQ ID NO 7
<211> LENGTH: 19
<212> TYPE: DNA
<213> ORGANISM: Artificial
<220> FEATURE:
<223> OTHER INFORMATION: PCR primer

<400> SEQUENCE: 7
caatgcagcc ggtctcatg                                                  19

<210> SEQ ID NO 8
<211> LENGTH: 24
<212> TYPE: DNA
<213> ORGANISM: Artificial
<220> FEATURE:
<223> OTHER INFORMATION: PCR primer

<400> SEQUENCE: 8
tctcccactt ttcgtagcta aacc                                            24

<210> SEQ ID NO 9
<211> LENGTH: 25
<212> TYPE: DNA
<213> ORGANISM: Artificial
<220> FEATURE:
<223> OTHER INFORMATION: PCR primer

<400> SEQUENCE: 9
aggagctctt agtgaccaag tgaag                                           25

<210> SEQ ID NO 10
<211> LENGTH: 22
<212> TYPE: DNA
<213> ORGANISM: Artificial
<220> FEATURE:
```

-continued

```
<223> OTHER INFORMATION: PCR primer

<400> SEQUENCE: 10
cccacaccat ccacaaagta tg                                              22

<210> SEQ ID NO 11
<211> LENGTH: 18
<212> TYPE: DNA
<213> ORGANISM: Artificial
<220> FEATURE:
<223> OTHER INFORMATION: PCR primer

<400> SEQUENCE: 11
ccctgcgtgg aggtggtt                                                   18

<210> SEQ ID NO 12
<211> LENGTH: 23
<212> TYPE: DNA
<213> ORGANISM: Artificial
<220> FEATURE:
<223> OTHER INFORMATION: PCR primer

<400> SEQUENCE: 12
atatgcccca tcttcaattg tct                                             23

<210> SEQ ID NO 13
<211> LENGTH: 21
<212> TYPE: DNA
<213> ORGANISM: Artificial
<220> FEATURE:
<223> OTHER INFORMATION: PCR primer

<400> SEQUENCE: 13
ggaggatacg aagcgttttc g                                               21

<210> SEQ ID NO 14
<211> LENGTH: 16
<212> TYPE: DNA
<213> ORGANISM: Artificial
<220> FEATURE:
<223> OTHER INFORMATION: PCR primer

<400> SEQUENCE: 14
accgggccac cctgat                                                     16
```

METHOD FOR PREDICTING THE RESPONSE TO A THERAPY

CROSS REFERENCE TO RELATED APPLICATIONS

This application is a 35 USC §371 National Stage application of International Application No. PCT/SE2008/051446 filed Dec. 12, 2008, now pending; which claims the benefit under 35 USC §119(a) to Sweden Application Ser. No. 0702789-9 filed Dec. 14, 2007. The disclosure of each of the prior applications is considered part of and is incorporated by reference in the disclosure of this application.

TECHNICAL FIELD

The present invention relates to the diagnosing and treatment of steroid resistant or steroid dependent diseases or disorders. The invention relates to a method for predicting the response to a therapy and for selecting a therapy, particularly for deciding on the applicability of a re-sensitization therapy. The invention is based on in vitro determination of the expression level of one or more marker gene(s) in a sample from a patient presenting with a disease or disorder related to steroid resistance or steroid dependence. The method may be applied to identifying marker genes useful in the method. The invention also discloses reagents and test kits for use in said method as well as methods for selecting an efficient therapy for said patient.

BACKGROUND

Natural glucocorticoids are steroid hormones that regulate a variety of biological processes and influence many physiological functions by virtue of their diverse roles in the growth, development, differentiation, and maintenance of basal and stress-related homeostasis (Munck, 1984; Clark, 1992). Glucocorticoids affect probably every organ in the mammalian body, yet many of their effects are specific for certain cell types or tissues. In addition, synthetic glucocorticoids are among the most widely prescribed drugs worldwide, used primarily as anti-inflammatory and immunosuppressive agents.

Steroid resistance or steroid dependence is still a major clinical concern for a large number of patients afflicted with inflammatory diseases as current therapies rely on the use of potent immunomodulators that can induce serious side-effects. Abnormalities in glucocorticoid sensitivity can be divided into 2 major groups: resistance and hypersensitivity. Resistance to glucocorticoids is characterized by the inability of organism or target tissues to respond to steroid molecules and can be generalized or tissue-specific, transient or permanent, partial or complete, and compensated or non-compensated (Chrousos, 1982; Chrousos, 1993). Complete glucocorticoid resistance is not compatible with life, given that absence of functional glucocorticoid receptors (GRs) in GR−/−knockout mice leads to severe neonatal respiratory distress syndrome and death within a few hours after birth (Cole, 1995).

Treatment with glucocorticoids is the most potent therapy available for acute and chronic asthma especially for patients with severe disease. Unfortunately, a certain fraction of asthmatics are steroid resistant (SR) and do not benefit from standard treatment. A rough estimate is that SR asthma occurs in approximately 15-20% of the asthmatic population. It is critical to identify these patients as early as possible. Patients who do not respond to low steroid doses are often placed on higher doses, which in SR asthmatics can cause significant adverse effects without providing significant benefit (Leung, 1995).

Inflammatory disorders normally treated with the natural or synthetic glucocorticoids, comprise asthma, rheumatoid arthritis, ulcerative colitis, Crohn's disease and other disorders. An inflammatory disorder includes complex diseases, which involve many factors and cell types and have a distinct inflammatory cytokine profile. The nature and magnitude of an immune response is largely dictated by the profile of the foreign antigen to which the immune system has been exposed. This event sets into motion a series of events that ultimately lead to the generation of humoral and cell-mediated immunity. These two different effector functions are brought about by the presence of two subpopulations of helper T cells (Th1 and Th2). Under "normal" healthy conditions, there is a delicate balance between the cytokines produced by the cell types Th1 and Th2. If this balance is lost, there will be a polarization resulting in predominantly Th1 or Th2 type inflammation and clinical manifestation of the disease will occur. As also indicated, different inflammatory diseases can be segregated as being either Th1 or Th2, depending on the cytokine profile seen. The cytokine picture indicates that asthma and ulcerative colitis are Th2 type diseases, while rheumatoid arthritis is associated with a Th1 type of inflammation.

New therapeutics have been applied to restore the "inbalance" in Th1 type diseases by reducing the cytokine profile of Th1 and thereby allowing an increase of the Th2 profile (Neurath et al., 1995; Mannon et al., 2004). The bacterial DNA has been shown to have immune stimulatory effects capable of activating B cells and natural killer cells (reviewed in Krieg, 1998) due to the presence of unmethylated CpG dinucleotides (CpG motifs). The vertebrate immune system has evolved the ability to recognize unmethylated CpG motifs and respond with a rapid and coordinated cytokine response leading to the induction of humoral and cell-mediated immunity (Krieg, 1996). For example, human and mouse cells respond to oligonucleotides containing a CpG motif by enhanced secretion of interferon-gamma (IFN-gamma) (Iho et al., 1999: Cowdery et al., 1996), IL-1, IL-6, IL-12 and tumor necrosis factor alpha (TNF-alpha) (Stacey et al., 1996; Jakob et al., 1998; Sparwasser et al., 1998). Due to the nature of cytokines induced, CpG containing oligonucleotides are largely considered to induce a Th1 profile both in vitro and in vivo (Zimmermann et al., 1998; Kline, 2000). In addition to the presence of CpG motifs, researchers have also noted that synthesizing CpG oligonucleotides with a full nuclease-resistant phosphorothioate backbone can potentate the stimulatory effects of the oligonucleotides, probably via stimulation of B-cells, whereas the same sequence with native phosphodiester backbone had no effect (Zhao et al., 1996).

The use of CpG motifs containing oligodeoxynucleotides (ODNs), or DNA vaccination which induce allergen-specific or unspecific Th1 responses are currently considered as a strategy both for the prevention and therapy of asthma (Wolleben, 2006).

The international patent application WO 2007/004977 concerns the treatment of a steroid refractory or steroid dependent patient afflicted with an inflammatory condition not responding or responding poorly or inadequately to a given anti-inflammatory treatment. The steroid efficacy can be enhanced by administering an effective amount of an oligonucleotide having the sequence 5'-Xm-CG-Yn-3' to the patient. In the sequence of the oligonucleotide X is A, T, C or G, Y is A, T, C or G, m=1- 100, n=1-100 and at least one CG dinucleotide is unmethylated.

The international patent application WO 2007/004979 concerns a method for enhancing the steroid efficacy in a steroid refractory or steroid dependent patient afflicted with an inflammatory condition not responding or responding poorly or inadequately to a given anti-inflammatory treatment by administering an effective amount of an oligonucleotide having the sequence 5'-TTCGT-Yn-3' to the patient. In the oligonucleotide sequence, X is A, T, C or G, Y is A, T, C or G, m=1-7, n=1-7 and at least one CG dinucleotide is unmethylated.

The above methods are applicable also in a situation, where weaning down the dosing of the anti-flammatory treatment is ineffective. Another therapy involving the use of oligonucleotides is presented in the international application WO 2002/085308, which discloses compositions, formulations, and kits for the treatment of respiratory and pulmonary diseases including asthma, infectious diseases, cancer and diseases having secondary effects on the lungs. This indicates that the compositions containing both anti-sense oligonucleotides and steroid agents and/or ubiquinones have effects superior to each agent alone and may be used as preventative, prophylactic or therapeutic single therapies or in conjunction with other therapies. The anti-sense oligonucleotide preferably contains about 0-15% of adenosine (A) and is anti-sense to the initiation codon, the coding region, the 5'-end or the 3'-end genomic flanking regions, the 5' or 3' intron-exon junctions, or regions within 2-10 nucleotides of the junctions of at least one gene regulating or encoding a target polypeptide associated with lung or airway dysfunction or cancer, or that is anti-sense to the corresponding mRNA.

The multi-gene approach disclosed in the international patent application WO 2004/001073, provides specific marker genes, which allow discrimination of inflammatory bowel disease, ulcerative colitis and Crohn's disease. The method compares gene expression profiles in biopsy samples obtained from inflamed, and optionally also from non-inflamed, areas in the intestines.

U.S. 20040197786 presents a method for examining steroid responsiveness in atopic dermatitis patients. In the method the expression levels of the genes RING6 and HLA-DMB are suggested as markers for testing steroid responsiveness and for use in the screening for compounds that may be used to improve steroid responsiveness.

The international patent application WO2003/021261 concerns a method for predicting the efficacy of a drug for treating an inflammatory disease, by analyzing the gene expression profile in a sample isolated from the patient.

Steroid dependency and steroid resistance does also occur in other conditions, such as steroid dependent nephrotic syndrome (SDNS), steroid-dependent corneal inflammation, edema of various etiology etc.

Despite the multitude of available therapies, the individual variations to said therapies remains a challenge to a physician confronting a patient presenting with syndromes related to a disease with no response or a poor response to a given steroid therapy. It would be advantageous for a physician dealing with said problems to have a simple and rapid in vitro test, which would enable a relatively reliable prediction of the response of the individual patient to the chosen therapy.

Therefore, there is a great demand for a simple, straightforward and rapid in vitro method for predicting steroid efficacy in a steroid unresponsive individual and to determine if the steroid efficacy in a steroid unresponsive, i.e. steroid resistant or steroid dependent individual can be enhanced. A method for predicting the response would simplify the choice of anti-inflammatory treatment, help to ameliorate the disease in question and decrease the costs and detrimental side effects of the steroid therapy, thereby increasing the quality and length of life for a large number of patients.

SUMMARY

The present invention relates to steroid resistant or steroid dependent disorders or diseases, and in particular to an in vitro method for selecting a therapy for a patient suspected of being steroid resistant or steroid dependent, or predicting the response of said patient presenting, wherein the method comprises determining the expression level of at least one potentially useful marker gene from cells, isolated from a sample of said patient and cultivated in the presence of a steroid, an immunomodulatory oligonucleotide or a mixture thereof. Said expression levels are compared to the expression level obtained in the absence of the steroid, immunomodulatory oligonucleotide or a mixture thereof and to a control, for example but not limited to the corresponding expression levels obtained with said marker gene from cells isolated from samples of volunteering healthy persons.

The method may also be used for identifying genes, which are potentially useful as marker genes for in vitro selection of an effective therapy for a steroid resistant patient or for predicting the responsiveness of said patient to different therapies. Applicable marker genes may be identified among genes involved in steroid response in a patient with an inflammatory condition. The genes selected to be used in the method are genes which provide expression levels in isolated cells cultivated in the presence or absence of selected therapeutic agents, which expression levels using statistical methods are significantly different in cells from patients as compared to cells from healthy persons or from steroid sensitive persons.

The present invention also relates to a test kit for selecting a therapy for a steroid resistant patient presenting with inflammatory symptoms, wherein said test kit comprises specific primer pairs for enabling in vitro analysis of expression level of at least one marker gene and instructions for use.

The invention also relates to the kit for determining steroid responsiveness of a steroid resistant patient or a patient with a poor steroid response and whether this steroid responsiveness could be enhanced by administration of an immunomodulatory oligonucleotide therapy, and to the use of the method and the kit in a therapy of a steroid resistant patient or a patient with a poor steroid response.

One embodiment of the invention is an in vitro method for selecting the therapy for a steroid resistant patient, for example a patient presenting with inflammatory symptoms, wherein the method comprises
  isolating cells from a sample taken from said patient;
  cultivating said isolated cells in the presence of a steroid, an immunomodulatory oligonucleotide or a mixture thereof;
  determining an expression level of at least one marker gene in said isolated cells; and
  comparing said expression level of said at least one marker gene to a value obtained from the cultivation of cells from a healthy person in the presence of a steroid, an immunomodulatory oligonucleotide or a mixture thereof, or to a normalized value obtained from a healthy population.

According to an embodiment of the above method, a significant similarity in the expression level of at least one selected marker gene measured in cells isolated from a sample of a steroid resistant patient and a healthy person, which cells are cultivated in the presence of a steroid, indicates that the selected marker gene is a potential marker for steroid responsiveness, and the results obtained are evaluated and used for selecting the therapy for said patient.

Further, according to another embodiment of the above method, a significant similarity in the expression levels of at least one selected marker gene measured in cells isolated from a sample of a steroid resistant patient and a healthy person, which cells are cultivated in the presence of a steroid and an immunomodulatory oligonucleotide, indicates that the selected marker gene is a potential marker for re-sensitization to the action of steroids.

According to another embodiment of the above method, a significant difference in the expression levels of at least one selected marker gene in cells isolated from a sample of a steroid resistant patient and a healthy person, which cells are cultivated in the presence of a steroid and an immunomodulatory oligonucleotide, indicates that the selected marker gene is a potential marker for steroid resistance, which may not be enhanced by the addition of an immunomodulatory oligonucleotide.

According to an embodiment of the above method, the selected marker gene or genes providing significantly different expression levels are one or more chosen from the genes CD163, Tsp1, IL1-R2, TLR2, TLR4, MKP1 and TXK.

According to an embodiment of the above method, an elevated expression level of at least one of the selected marker genes in cells isolated from a sample of the patient and cultivated in the presence of a steroid as compared to the expression level in the absence of the steroid, indicates that the patient would benefit from a steroid therapy. Preferably, the selected marker gene or genes is/are at least one of the genes CD163, Tsp1, and IL1-R2.

According to an embodiment of the above method, an elevated expression level, and preferably a dose-dependent increase, of at least one of the selected marker genes in cells isolated from a sample of the patient and cultivated in the presence of a steroid and an immunomodulatory oligonucleotide as compared to the expression level in absence of said steroid and immunomodulatory oligonucleotide, indicates that the patient would benefit from a combination therapy. Preferably, the selected marker gene or genes is/are at least one of the genes CD163, Tsp1, and IL1-R2.

According to an embodiment of the invention, a significant difference in expression levels of at least one marker gene measured in isolated cells from a sample of a steroid resistant patient and healthy person and cultivated in the presence of a steroid and an immunomodulatory oligonucleotide, indicates that said steroid resistant patient would benefit from being excluded from a steroid therapy and being subjected to an alternative therapy comprising an immunomodulatory oligonucleotide therapy. Here, the selected marker genes are preferably chosen from CD163, Tsp1, IL1-R2, TLR2, TLR4, MKP-1 and TXK.

In the inventive method, the cell is preferably a blood cell, and more preferably a peripheral blood mononuclear cell (PMBC).

The methods according to the invention are applicable to all conditions, where a patient exhibits steroid resistance or dependence. A skilled person will be able to identify conditions, where it would be valuable to determine if a patient is steroid dependent or resistant, and if said patient would benefit from a specific therapy.

The invention is particularly drawn towards patients presenting with inflammatory symptoms, and most particularly, the inflammatory symptom is an inflammatory symptom chosen from acute or chronic asthma, chronic obstructive pulmonary disease (COPD), ulcerative colitis, Crohn's disease, rheumatoid arthritis, psoriasis, and emphysema.

The therapy concerned may be a combination therapy or an alternative therapy comprising e.g. the administration of an immunomodulatory oligonucleotide. Preferably the combination therapy includes the administration of a steroid and an immunomodulatory oligonucleotide.

The term "steroid" is used to encompass both corticosteroids and glucocorticosteroids. The steroid can be chosen from but is not limited to beclomethasone, prednisolone, methylprednisolone, fluticasone, triamcinolone, budesonide or dexamethasone, including equivalent drugs.

In the various embodiments of the invention, the steroid is a glucocorticoid, preferably a synthetic glucocorticoid, such as hydrocortisone, prednisone, prednisolone, methylprednisolone, dexamethasone, betamethasone, triamcinolone, beclomethasone, fludrocortisones, deoxycorticosterone, and aldosterone, preferably dexamethasone.

According to an embodiment of the invention, the expression level of said marker gene is determined by nucleic acid amplification of said gene using gene specific primers, and quantifying the amplification results.

Preferably the nucleic acid amplification is performed by a real time PCR and using the gene specific primers chosen from SEQ ID NO: 1-7.

The invention also concerns a test kit for selecting a therapy for a steroid resistant patient presenting with inflammatory symptoms, wherein said test kit comprises specific primer pairs for enabling in vitro analysis of expression level of at least one marker gene and instructions for use.

In the above kit, said specific primer pairs are selected from the group of SEQ ID NO: 1-14 or functionally equivalent primer pairs specific for at least one of the genes CD163, Tsp1, IL1-R2, TLR2, TLR4, MKP1 and TXK.

In a particular embodiment, said specific primer pairs are SEQ ID NO: 1 and SEQ ID NO: 2 or functionally equivalent primer pairs specific for the CD163 marker gene.

A kit according to the invention may further preferably comprise means for cultivating cells, and an agent for sensitizing the cells to the action of steroids.

Said kit preferably further comprises means for carrying out hybridization or annealing assay.

The invention also concerns the use of a method as defined above for determining steroid responsiveness of a steroid resistant patient or a patient with a poor steroid response. Alternatively, the method is used for identifying a steroid resistant patient, who would benefit from an immunomodulatory oligonucleotide therapy. Alternatively, the method is used for screening whether an immunomodulatory compound enhances steroid responsiveness of a steroid resistant patient or a patient with poor steroid response.

The invention also discloses the use of any one of the genes CD163, Tsp1, IL1-R2, TLR2, TLR4, MKP1 and TXK, for preparing a reagent for in vitro identification of steroid responsive patients, which would benefit from steroid therapy; or for preparing a reagent for in vitro identification of steroid resistant patients, which would benefit from combination therapy comprising steroid therapy and immunomodulatory oligonucleotide therapy; or for preparing a reagent for in vitro identification steroid responsive patients, which would benefit from being excluded from steroid therapy; or for preparing a reagent for in vitro identification steroid resistant patients, which would benefit from being subjected to an alternative therapy comprising an immunomodulatory oligonucleotide therapy.

In the above, the reagent is preferably a primer pair specific for said genes.

More preferably, the reagent is an oligonucleotide probe, which is complementary to a specific region of said genes and capable of hybridizing or annealing with said genes.

Further aspects of the invention are set out in the attached claims, hereby incorporated by reference.

DESCRIPTION OF THE DRAWINGS

The invention will be described in closer detail in the description, examples and claims, with reference to the attached figures in which:

DETAILED DESCRIPTION

Figure 1:
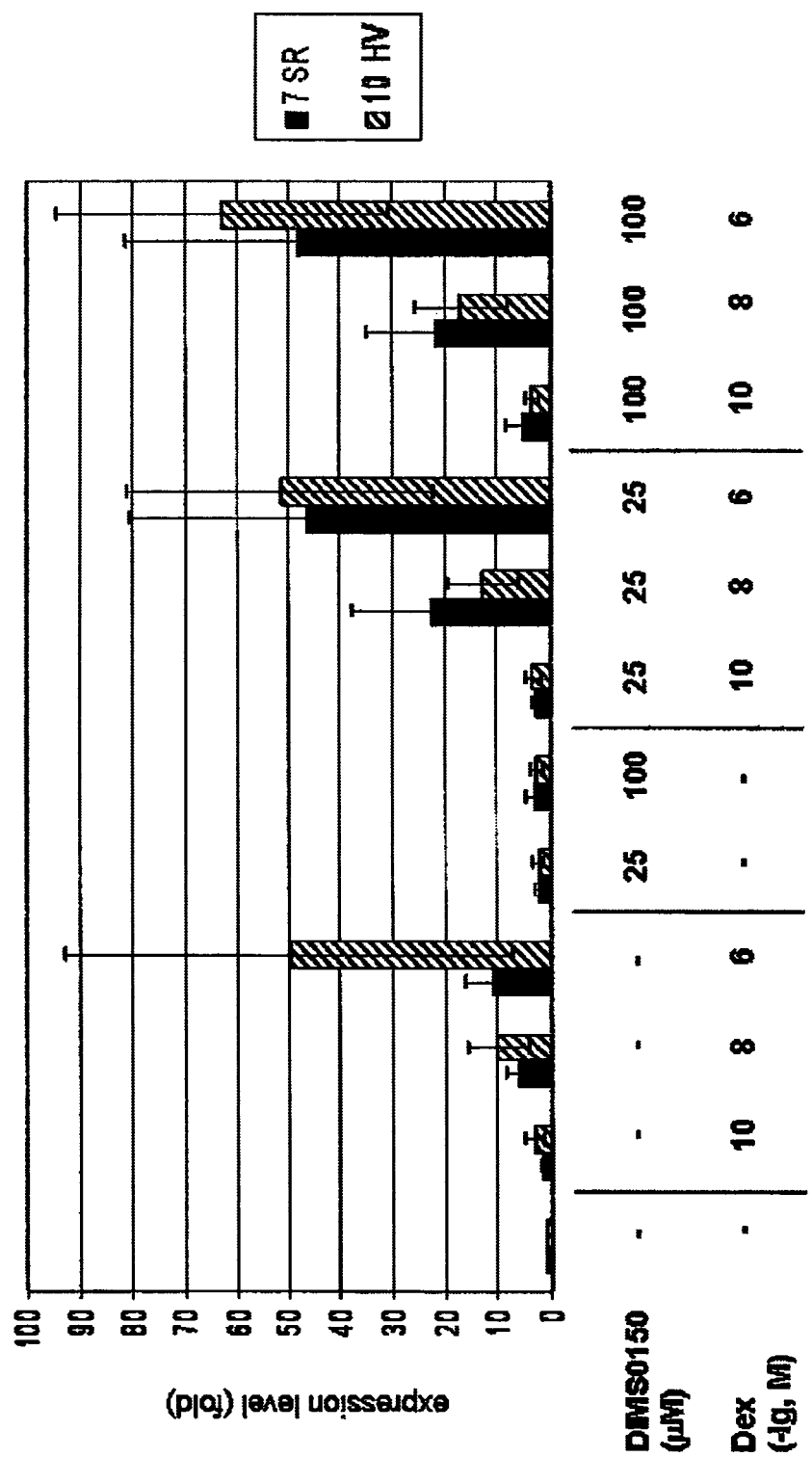
FIG. 1 depicts the average value of expression level of CD163 gene in peripheral blood mononuclear cells (PBMC) in response to 48 hrs stimulation with the immunomodulatory oligonucleotide IDX0150 alone, dexamethasone (Dex) alone, or IDX0150 and Dex in combination as quantified by real-time PCR. PBMC were isolated from blood samples of ten (n=10) healthy volunteers (HV) and seven (n=7) steroid resistant asthma patients (SR). Cells were incubated in a basal medium or in a basal medium with increasing concentrations of IDX0150 (25 µM or 100 µM) in the presence or absence of Dex at increasing concentrations ($10^{-10}$, $10^{-8}$ or $10^{-6}$ M) as described in Example 1. After incubation, the total RNA was isolated from PBMCs and used for first strand cDNA synthesis. Real-time PCR reactions with PBMC cDNA were performed in triplicates for each sample/treatment combination and in duplicates for a housekeeper gene (γ-actin). Each bar of the histogram represents the average expression level value, normalized by basal expression level value as described in Example 1. The error-bars indicate the deviation range of the values of expression levels in different blood donors.

Before the invention is decribed in detail, it is to be understood that this invention is not limited to the particular component parts of the devices described or the process steps of the methods described, as such devices and methods may vary. It is also to be understood that the terminology used herein is for purposes of describing particular embodiments only, and is not intended to be limiting.

It must be noted that, as used in the specification and the appended claims, the singular forms "a", "an", and "the" also include plural referents unless the context clearly dictates otherwise. Thus, for example, reference to "a sequence" includes more than one such sequence, and the like, In this specification and in the claims which follow, reference will be made to a number of terms which shall be defined to have the following meanings:

The term "about" is used to indicate a deviation of +/−2% of the given value, preferably +/−5% and most preferably +/−10% of the numeric values, when applicable.

The term "responsiveness" refers to a response of a patient or the cells obtained from the patient to a given agent or medicament. The term "steroid responsiveness" or "steroid response" describes the change of an immune response when challenged with a steroid. This change is measurable often through the release of certain cytokines such as interferons and interleukins as well as other physiological parameters such as proliferation. The response can equally be one that serves to stimulate the immune system as well as to repress the immune system depending on the cytokines induced by the steroid treatment in question. Patients whose symptoms are relieved by steroid administration are considered "steroid responsive". In contrast, patients in which administration of a steroid, typically effective in patients having such diseases and healthy persons, is ineffective, are considered "steroid resistant" or "steroid refractory" patients, which in the present invention include also patients who respond poorly or inadequately, i.e. exhibit only a slight effect or improvement of symptoms. Two types of steroid resistant patients have been described i.e. acquired steroid resistance (Type I) and primary steroid resistance (Type II), both of which are comprised in the present invention.

The determination of whether a patient is steroid refractory is difficult as no universally accepted method or indeed endpoint exists which can be used to assess such a condition. Moreover, steroid unresponsiveness is a dynamic scale and there are varying degrees of unresponsiveness. From a clinical perspective, the diagnosis of steroid unresponsiveness is often based on the physician's judgment and treatment history with steroids. For example, in IBD, increasing the dose of steroids for a certain period of time without achieving symptomatic relief may be indicative of a possible state of steroid unresponsiveness in that individual. In asthma, patients can be given a two week course of relatively high steroid doses, following which they undergo a lung function test. A performance below a certain threshold may suggest a steroid refractory state. The following references constitute examples, disclosing how the physician evaluates the treatment of the underlying disease and identifies steroid refractory patients (Reinisch et al., 2002; Munkholm et al., 1994; Leung et al., 2002; Gisbert et al., 2008).

Adrenocortical hormones or corticosteroids are steroid hormones classified as glucocorticoids, mineralocorticoids and sex hormones. Many of the clinically useful "steroids" are glucocorticoids or glucocorticosteroids, including cortisone, hydrocortisone, and their pharmaceutical derivatives such as prednisone and dexamethasone that exert their effect by binding to specific cytosolic receptors. Synthetic glucocorticoids with greater glucocorticoid activity have been developed, having increased affinity for the glucocorticoid receptors and/or delayed plasma clearance. Glucocorticoids are used primarily as "anti-inflammatory" and "immunosuppressive" agents. The term "anti-inflammatory" refers to the property of a substance or treatment that reduces symptoms of inflammation. "Immunosuppressive agent" refers to an agent that suppresses the cell-mediated immunity.

For purposes of the invention, the term "oligonucleotide" refers to a polynucleoside formed from a plurality of linked individual nucleoside units. Such oligonucleotides can be obtained from existing nucleic acid sources, including genomic or cDNA, but are preferably produced by synthetic methods. The nucleoside residues can be coupled to each other by any of the numerous known internucleoside linkages. Such internucleoside linkages include, without limitation, the natural internucleoside phosphodiester bond or indeed modified internucleosides such as, but not limited to, phosphorothioate, phosphorodithioate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages. The term "oligonucleotide" also encompasses polynucleosides having one or more stereospecific internucleoside linkage (e. g., (Rp)-or Sp)-phosphorothioate, alkylphosphonate, or phosphotriester linkages). As used herein, the terms "oligonucleotide" and "dinucleotide" are expressly intended to include polynucleosides and dinucleosides having any such internucleoside linkage, whether or not the linkage comprises a phosphate group.

The term "oligonucleotide" also encompasses polynucleosides having additional substituents including, without limitation, protein groups, lipophilic groups, intercalating agents, diamines, folic acid, cholesterol and adamantane. The term "oligonucleotide" also encompasses any other nucleobase containing polymer, including, without limitation, peptide nucleic acids (PNA), peptide nucleic acids with phosphate groups (PHONA), locked nucleic acids (LNA), morpholino-backbone oligonucleotides, and oligonucleotides having backbone sections with alkyl linkers or amino linkers.

The oligonucleotides contain naturally occurring nucleosides, modified nucleosides, or mixtures thereof. As used herein, the term "modified nucleoside" is a nucleoside that includes a modified heterocyclic base, a modified sugar moiety, or a combination thereof. In some embodiments, the modified nucleoside is a non-natural pyrimidine or purine nucleoside, as herein described. In some embodiments, the modified nucleoside is a 2'-substituted ribonucleoside an arabinonucleoside or a 2'-deoxy-2'-substituted-arabinoside.

The oligonucleotide used in the inventive method can be modified according to methods known for the skilled person and as defined above. For example, at least one nucleotide of the oligonucleotide can have a phosphate backbone modification, wherein the phosphate backbone modification is a phosphorothioate or phosphorodithioate modification. The modification can occur at one or more nucleotides at any position along the entire length of the oligonucleotide. In one embodiment the nucleic acid backbone includes the phosphate backbone modification on the 5' inter-nucleotide linkages. As an alternative the nucleic acid backbone includes the phosphate backbone modification on the 3' inter-nucleotide linkages.

The term "oligonucleotide" also includes hybrid and chimeric oligonucleotides. A "chimeric oligonucleotide" is an oligonucleotide having more than one type of internucleoside linkage within its sequence structure. One preferred example of such a chimeric oligonucleotide is a chimeric oligonucleotide comprising a phosphorothioate, phosphodiester or phosphorodithioate region and non-ionic linkages such as alkylphosphonate or alkylphosphonothioate linkages (Pederson et al. U.S. Pat. Nos. 5,635, 377 and 5,366,878).

A "hybrid oligonucleotide" is an oligonucleotide having more than one type of nucleoside. One preferred example of such a hybrid oligonucleotide comprises a ribonucleotide or 2'-substituted ribonucleotide region,and a deoxyribonucleotide region (Metelev and Agrawal, U.S. Pat. Nos. 5,652,355, 6,346,614 and 6,143,881).

For purposes of the invention, the term "immunomodulatory oligonucleotide" refers to an oligonucleotide as described above that induces an immune response either by stimulating the immune system or repressing the immune system or both in an organism when administered to a vertebrate, such as a mammal. As used herein, the term "mammal" includes, without limitation rats, mice, cats, dogs, horses, cattle, cows, pigs, rabbits, non-human primates, and humans.

Preferably, the "immunomodulatory oligonucleotide" comprises at least one naturally occurring phosphodiester, or one modified phosphorothioate, or phosphorodithioate internucleoside linkage, however preferred linkages or indeed backbone modifications including, without limitation, methylphosphonates, methylphosphonothioates, phosphotriesters, phosphothiotriesters, phosphorothioates, phosphorodithioates, triester prodrugs, sulfones, sulfonamides, sulfamates, formacetal, N-methylhydroxylamine, carbonate, carbamate, morpholino, boranophosphonate, phosphoramidates, especially primary amino-phosphoramidates, N3 phosphoramidates and N5 phosphoramidates, and stereospecific linkages (e. g., (Rp)-or (Sp)-phosphorothioate, alkylphosphonate, or phosphotriester linkages).

In some embodiments, the "immunomodulatory oligonucleotide" comprises an immunostimulatory dinucleotide of formula 5'-Pyr-Pur-3', wherein Pyr is a natural or synthetic pyrimidine nucleoside and Pur is a natural or synthetic purine nucleoside. In some preferred embodiments, the immunomodulatory oligonucleotide comprises an immunostimulatory dinucleotide of formula 5'-Pur*-Pur-3', wherein Pur* is a synthetic purine nucleoside and Pur is a natural or synthetic purine nucleoside. In various places the dinucleotide is expressed as RpG, C*pG or YZ, in which case respectively, R, C*, or Y represents a synthetic purine. A particularly preferred synthetic purine is 2-oxo-7-deaza-8-methyl-purine. When this synthetic purine is in the Pur* position of the dinucleotide, species-specificity (sequence dependence) of the immunostimulatory effect is overcome and cytokine profile is improved. As used herein, the term "pyrimidine nucleoside" refers to a nucleoside wherein the base component of the nucleoside is a monocyclic nucleobase. Similarly, the term "purine nucleoside" refers to a nucleoside wherein the base component of the nucleoside is a bicyclic nucleobase. For purposes of the invention, a "synthetic" pyrimidine or purine nucleoside includes a non-naturally occurring pyrimidine or purine base, a non-naturally occurring sugar moiety, or a combination thereof.

In some embodiments, the sugar moiety of the nucleoside can be a non-naturally occurring sugar moiety. For purposes of the present invention, a "naturally occurring sugar moiety" is a sugar moiety that occurs naturally as part of a nucleic acid, e. g., ribose and 2'-deoxyribose, and a "non-naturally occurring sugar moiety" is any sugar that does not occur naturally as part of a nucleic acid, but which can be used in the backbone for an oligonucleotide, for example, but not limited to, hexose. Arabinose and arabinose derivatives are examples of preferred sugar moieties.

Preferred "immunostimulatory moieties" according to the invention further include nucleosides having sugar modifications, including, without limitation, 2'-substituted pentose sugars including, without limitation, 2'-O-methylribose, 2'-O-methoxyethyl- ribose, 2'-O-propargylribose, and 2'-deoxy-2'-fluororibose; 3'-substituted pentose sugars, including, without limitation, 3'-O-methylribose; 1',2'-dideoxyribose; arabinose; substituted arabinose sugars, including, without limitation, 1'-methylarabinose, 3'-hydroxymethylarabinose, 4'-hydroxymethylarabinose, 3'-hydroxyarabinose and 2'-substituted arabinose sugars; hexose sugars, including, without limitation, 1,5-anhydrohexitol; and alpha-anomers.

In another embodiment, preferred "immunostimulatory moieties" according to the invention further include oligonucleotides having other carbohydrate backbone modifications and replacements, including peptide nucleic acids (PNA), peptide nucleic acids with phosphate groups (PHONA), locked nucleic acids (LNA), morpholino backbone oligonucleotides, and oligonucleotides having backbone linker sections having a length of from about 2 angstroms to about 200 angstroms, including without limitation, alkyl linkers or amino linkers. The alkyl linker may be branched or unbranched, substituted or unsubstituted, and chirally pure or a racemic mixture. Most preferably, such alkyl linkers have from about 2 to about 18 carbon atoms. In some preferred embodiments such alkyl linkers have from about 3 to about 9 carbon atoms. Some alkyl linkers include one or more functional groups selected from the group consisting of hydroxy, amino, thiol, thioether, ether, amide, thioamide, ester, urea, and thioether. Some functionalized alkyl linkers are poly (ethylene glycol) linkers of formula-0-(CH2—CH2—O—), (n=1-9). Some other functionalized alkyl linkers are peptides or amino acids.

In a further embodiment preferred "immunostimulatory moieties" according to the invention further include DNA isoforms, including, without limitation, -L-deoxyribonucleosides and a-deoxyribonucleosides. Preferred immunostimulatory moieties according to the invention incorporate 3' modifications, and further include nucleosides having unnatural internucleoside linkage positions, including, without limitation, 2'-5', 2'-2', 3'-3' and 5'-5' linkages The "immunomodulatory oligonucleotide" according to the invention comprise at least five nucleosides linked via internucleoside linkage or a functionalized nucleobase or sugar via a non-nucleotidic linker. For purposes of the invention, a "non-nucleotidic linker" is any moiety that can be linked to the oligonucleotides by way of covalent or non-covalent linkages.

Non-covalent linkages include, but are not limited to, electrostatic interaction, hydrophobic interactions, -stacking interactions, and hydrogen bonding. The term "non-nucleotidic linker" is not meant to refer to an internucleoside linkage, as described above, e. g. a phosphodiester, phosphorothioate, or phosphorodithioate functional group that directly connects the 3'-hydroxyl groups of two nucleosides. For purposes of this invention, such a direct 3'-3' linkage (no linker involved) is considered to be a "nucleotidic linkage."

In some embodiments, the non-nucleotidic linker is a metal, including, without limitation, gold particles. In some other embodiments, the non-nucleotidic linker is a soluble or insoluble biodegradable polymer bead. In yet other embodiments, the non-nucleotidic linker is an organic moiety having functional groups that permit attachment to the oligonucleotide. Such attachment preferably is by any stable covalent linkage. In some embodiments, the non-nucleotidic linker is a biomolecule, including, without limitation, polypeptides, antibodies, lipids, antigens, allergens, and oligosaccharides. In some other embodiments, the non-nucleotidic linker is a small molecule. For purposes of the invention, a small molecule is an organic moiety having a molecular weight of less than 1,000 Da.

In some embodiments, the small molecule is an aliphatic or aromatic hydrocarbon, either of which optionally can include, either in the linear chain connecting the oligonucleotides or appended to it, one or more functional groups selected from the group consisting of hydroxy, amino, thiol, thioether, ether, amide, thioamide, ester, urea, and thiourea. The small molecule can be cyclic or acyclic. Examples of small molecule linkers include, but are not limited to, amino acids, carbohydrates, cyclodextrins, adamantane, cholesterol, haptens and antibiotics. However, for purposes of describing the non-nucleotidic linker, the term "small molecule" is not intended to include a nucleoside.

In some embodiments, the small molecule linker is glycerol or a glycerol homolog of the formula HO—(CH2)o-CH(OH)—(CH2)p-OH, wherein o and p independently are integers from 1 to about 6, from 1 to 4, or from 1 to 3. In some other embodiments, the small molecule linker is a derivative of 1,3-diamino-2-hydroxypropane. Some such derivatives have the formula HO—(CH2)m-C(O)NH—CH2-CH(OH)—CH2-NHC(O)-m-OH, wherein m is an integer from 0 to about 10, from 0 to 6, from 2 to 6, or from 2 to 4.

Modified or substituted oligonucleotides are often preferred over native forms because of desirable properties such as, for example, enhanced cellular uptake, enhanced affinity for nucleic acid target and increased stability in the presence of nucleases. An oligonucleotide is usually comprised of more than two (2), and typically more than ten (10) and up to one hundred (100) or more deoxyribonucleotides or ribonucelotides, although preferably between about eight (8) and about forty (40), most preferably between about eight (8) and about twenty (20). The exact size will depend on many factors, which in turn depends on the ultimate function or use of the oligonucleotide. The oligonucleotide may be generated in any manner, including chemical synthesis, DNA replication, reverse transcription, or a combination thereof.

The term "CpG containing oligonucleotide" is used to encompass an oligonucleotide having at least one unmethylated CG dinucleotide within its entire sequence length and being preferably 8 to 100 nucleic acid bases in length.

The present inventors, who had previously demonstrated a rapid and pronounced improvement of the patients and reduction in the dose of steroids when providing patients suffering from an inflammatory condition of bowel, including ulcerative colitis and Crohn's diseases and not responding to steroid therapies, with an immunomodulatory oligonucleotide containing a CpG motif together with a steroid, recognized that it would be advantageous to have a marker gene, which could be used for predicting the responsiveness of a patient to a selected therapy. The present inventors demonstrated a correlation between the expression levels of some selected marker genes and the response to a given therapy. The present invention therefore is related to a rapid and easy in vitro method for predicting the response of a therapy and particularly selecting an effective therapy for a steroid resistant patient suffering from an inflammatory condition. The therapy in question is either a combination therapy comprising a steroid and an immunomodulatory oligonucleotide therapy or an alternative therapy comprising an immunomodulatory oligonucleotide combined with another therapy.

The first objective of the invention was to identify steroid responsive genes that would act as potential marker genes for re-sensitization of steroid resistant asthma patients to the action of steroids as well as potential markers for resistance of asthma patients to steroid treatment when compared to expression of these genes in healthy. In other words, the objective of the present invention was to identify genes, which by an easy and rapid in vitro method would discriminate between steroid sensitive and steroid resistant asthma patients and also candidate genes that are indicative of a possible positive response in a steroid resistant patient when given an immunomodulatory oligonucleotide containing an unmethylated CpG motif, such as the IDX0150 or IDX0150 compound. Such patient would be responsive to a so called re-sensitization therapy.

The selected marker genes would be useful in selecting the best therapy for steroid resistant patients or patients with a poor steroid response.

The present invention relates to an in vitro method for selecting the therapy for a steroid resistant patient presenting with inflammatory symptoms, wherein the method comprises comparing expression levels of at least one potentially useful marker gene from cells, which are isolated from a sample of said patient and a healthy person, and which cells are cultivated in the presence of a steroid, an immunomodulatory oligonucleotide or a mixture thereof.

In one embodiment of the present invention relates to a method for determining "steroid efficacy" in a steroid refractory patient afflicted with an inflammatory condition not responding or responding poorly or inadequately to anti-inflammatory treatment, and predicting if this "steroid efficacy" may be enhanced by administration of an immunomodulatory oligonucleotide having the sequence $$5'-Xm-CG-Yn-3'$$

is administered in an effective amount to said patient and wherein X is A, T, C or G, Y is A, T, C, or G, m=1-100, n=1-100 and wherein at least one CG dinucleotide is unmethylated. Alternatively, the immunomodulatory oligonucleotide may have the sequence $$5'-Xm-TTCGT-Yn-3$$

wherein X is A, T, C or G, Y is A, T, C, or G, m=1-7, n=1-7 and wherein at least one CG dinucleotide is unmethylated.

The term "inflammatory symptoms" or "inflammatory condition" are used to mean the same in the present invention and refer to the first response of the immune system to infection or irritation and may be referred to as the innate immune system. Inflammation helps to fight disease, but in the long term it causes progressive damage. The nature and magnitude of an immune response is largely dictated by the profile of the foreign antigen to which the immune system has been exposed. This event sets into motion a series of events that ultimately leads to the generation of humoral and cell-mediated immunity. Inflammatory diseases comprise such as acute or chronic asthma, chronic obstructive pulmonary disease (COPD), ulcerative colitis (UC), Crohn's disease (CD), rheumatoid arthritis, psoriasis and emphysema. In a preferred embodiment the inflammatory condition is asthma.

Genetic expression of a "marker gene" changes in response of tissue or cell culture to administration of a pharmacological agent, progression of cell differentiation, or in response to changes in environmental conditions. Quantifying expression of a marker gene therefore has predictive potential particularly in medical diagnostics.

The term "expression level" refers to intensity of transcription of a target gene into messenger RNA (mRNA) under different experimental or environmental conditions and subsequent translation into a protein. Gene expression corresponds to the number of copies of mRNA that exists for a particular gene. In living cells gene expression is controlled by transcription factors binding to the regulatory regions of a gene. The genes can be inducible, i.e. resulting in increase in the amount of mRNA, or constitutively expressed, i.e. having a constant amount of mRNA under different conditions. Methods to analyse the quality and quantity of the transcribed mRNA are described in the several laboratory handbooks (for example, in Sambrook and Russell, 2001) and are well known for a person skilled in the art. These methods comprise ribonuclease protection, primer extension, northern blotting, dot blot hybridization, and conventional or real time PCR.

Traditionally, the amount of a particular mRNA produced, and thus the activation status of a gene has been measured by northern blotting. Total RNA isolated from a sample is separated by agarose gel electrophoresis, and probed with a complementary DNA probe specific for the gene of interest. In conventional polymerase chain reaction (PCR), the total RNA isolated from the cell or tissue to be analyzed is reverse transcribed into first strand cDNA (RT-PCR), which is then used as a template to amplify a double stranded amplicon with target specific oligonucleotide primers. In both techniques detection is based on detectable labels, such as fluorescent dyes or radioactive isotopes. Also the recently developed techniques known as DNA chips or microarrays are based on hybridization the target DNA to complementary target specific primers, washing out the unbound DNA and quantifying the bound target DNA. Probes and primers used in the hybridization reactions may be designed based on the nucleotide sequence of the marker gene or amino acid sequence of the translated protein, corresponding to the marker gene. A convenient quantitative hybridization method for determining variations in the amounts of expressed RNA is described in the international patent application WO 2002/055734.

Preferably, the "marker gene expression" may be quantified with real time PCR, also called quantitative real time PCR. The method follows the general pattern of polymerase chain reaction, but the amplified region of the target DNA is quantified after each round of amplification by using fluorescent dyes, such as SYBR Green that intercalate with double-stranded DNA or modified DNA oligonucleotide probes that fluoresce when hybridized with a complementary DNA. Frequently, real time PCR is combined with reverse transcription to quantify low abundance mRNA. The data can be analysed by computer software, such as Applied Biosystems 7500 or 7500 Fast Real Time PCR Systems, to calculate relative gene expression between several samples, or mRNA copy number based on a standard curve. Relative quantification (RQ) is commonly used to compare expression levels of wild-type with mutated alleles or the expression levels of a gene in different tissues. RQ determines the change in expression of a target gene in a test sample relative to the same sequence in a basal or calibrator sample (a sample used as the basis for comparative results). The calibrator sample can be an untreated control or a sample at time zero in a time-course study. By using an endogeneous or intrinsic control, it is possible to normalize quantification of a cDNA target for differences in the amount of cDNA added to each reaction. Typically, housekeeping genes such as β-actin, glyseraldehyde-3-phosphate dehydrogenase (GAPDH) and ribosomal RNA (rRNA) are used as endogeneous controls, because their expression levels are relatively stable. Replicate reactions per sample and an endogenous control are needed to ensure statistical significance.

The expression levels in the samples from a steroid resistant patient and a patient with poor steroid response may be compared by determining the expression intensity of the marker gene as described above or by analyzing the protein translated from the marker gene, i.e. a marker protein utilizing, for example antibodies binding to the marker protein. The binding can be detected by techniques such as western blotting, flowcytometry, immunoprecipitation and ELISA. Also, response to a given treatment can be quantified by measuring activity of the marker protein in case the gene product is a functional protein, for example an enzyme. Alternatively, the comparative analysis of different mRNA splicing variants of the marker gene, which have been shown to be translated into different forms of the marker protein and having different predominance in cells of a healthy person and a patient presenting with inflammation symptoms, may be used to predict the effect of steroid therapy.

In one embodiment of the present invention the marker genes useful in the method for selecting the therapy for a steroid resistant patient may be identified among genes, which are involved with steroid response in inflammatory conditions. The genes selected are preferably genes, which provide significantly different expression levels in cells isolated from samples of patients and healthy persons.

Selection of the potentially useful marker genes may be performed based on a database and literature search for known genes related to the steroid response in the specific inflammatory conditions. Alternatively such marker genes may be defined by a screening approach, in which the expression level of a multitude of genes is determined by methods such as real time PCR or methods using DNA chips or DNA microarrays or by screening cDNA libraries prepared from steroid resistant patients and healthy persons. The number of potential marker genes may vary depending on the information available and/or the chosen method to determine the expression levels.

Many experiments in cellular biology are conducted outside organisms or cells, i.e. "in vitro", in a controlled environment such as in a test tube in contrast to in vivo tests, which are used only to verify the results of the method of the present invention. The "in vitro" conditions are suited for deducing the mechanisms of action. The in vitro determination is carried out by determining the expression levels or relative expression profiles obtained using cells isolated from patients and healthy person and cultivated in the presence or absence of selected therapeutic agents. The effects found by these in vitro methods may be tested inside living organisms, using not only cells, but also animal experiments before making the final conclusions and verifying the results in a clinical test.

The response to a given treatment may be determined by cultivating the cells isolated from a biological sample, such as a biopsy sample or blood sample from a steroid resistant patient and a healthy person. The preferred peripheral blood mononuclear cells (PBMC) of the present invention may be isolated from a heparinized blood sample by a density gradient centrifugation. Said cells are cultivated in a suitable buffered cultivation medium containing required salts, vitamins, hormones and trace elements to keep the cells alive and for their growth and differentiation. The PBMC are cultivated in a RPMI medium for 48° C. in a presence of a steroid, an immunomodulatory oligonucleotide or a mixture thereof, and the expression level of potential marker genes is determined using methods described above. Finally, the expression levels of particular marker genes in cells of said patients and healthy persons, treated as described above are statistically compared.

The terms "significant similarity" and "significant difference" means that using statistical methods the expression levels measured in cultivated cells isolated from steroid resistant patients and healthy persons are almost identical or are clearly different, when they are cultivated and grown in the presence or absence of the tested therapeutic agents. These significant similarities or differences may be used for predicting the responses of the patient and selecting appropriate therapies.

In one embodiment of the invention a "significant similarity" in the expression levels of at least one selected marker gene measured in cells isolated from a sample of a steroid resistant patient and a healthy person, which cells are cultivated in the presence of a steroid, indicates that the selected marker gene is a potential marker for steroid responsiveness.

In another embodiment of the invention a significant similarity in the expression levels of at least one selected marker gene measured in cells isolated from a sample of a steroid resistant patient and a healthy person, which cells are cultivated in the presence of a steroid and an immunomodulatory oligonucleotide, indicates that the selected marker gene is a potential marker for re-sensitization to the action of steroids.

The term "re-sensitization" means that cells, which should be sensitive or susceptible to a given stimulatory drug, but have lost that property, may again through a sensitization therapy become sensitive or susceptible to said stimulatory drug.

The expression "enhance steroid efficacy" or "steroid enhancing effect" is here used to encompass a steroid sparing effect, evident as a clinical picture where a simultaneous or sequential treatment with an immunomodulatory oligonucleotide, preferably a pre-treatment, is shown to reduce the steroid dose necessary to manage inflammation or improve the symptoms faster. The expression "enhance steroid efficacy"

is also intended to encompass a synergistic use of an immunomodulatory oligonucleotide and a steroid, either simultaneously or substantially simultaneously, or sequentially or substantially sequentially, shown to reduce the steroid dose necessary to manage inflammation or to relieve the symptoms of the patient faster than without an immunomodulatory administration.

In a further embodiment of the invention a "significant difference" in the expression levels of at least one selected marker gene in cells isolated from a sample of a steroid resistant patient and a healthy person, which cells are cultivated in the presence of a steroid and an immunomodulatory oligonucleotide, indicates that the selected marker gene is a marker gene for steroid resistance, which may not be enhanced by the addition of an immunomodulatory oligonucleotide.

The meaning of the term "significant" or "significantly" is that understood by a skilled person, and determined using a statistical test such as, but not limited to Student's t-test, Dunnett's test or Bonferroni test.

The candidate genes for developing an in vitro assay of the present invention were selected based on a database and literature search for known genes related to human PBMC steroid response. Such genes have been described by several research groups (Galon et al., 2002, Vermeer et al., 2004, Shahidi, 1999, Mariette, 2003, Wu et al., 2004). The present inventors chose seven genes. These genes include one member of interleukin 1 signaling pathway (IL1-R2), one member of macrophage scavenger receptor family (CD163), a matrix glycoprotein thrombospondin-1 (Tsp1), two members of Toll-like receptors family (TLR2 and TLR4) and two enzymes (TXK and MPK-1). The anti-inflammatory IL1-R2 receptor (Galon et al., 2002; Mariette, 2003) is a member of interleukin 1 (IL1) signaling pathway recognizing, for example the cytokines IL1α and IL1β and IL1 receptor antagonist. Glucocorticoids have been shown to up-regulate IL1-R2 gene expression (Re 1994; Galon et al., 2002).

CD163, also called M130, (Galon et al. 2002) is a member of macrophage scavenger receptor family expressed in blood mononuclear cells and most tissue macrophages. The function of CD163 in inflammation may depend on the presence of different mRNA splicing variants that may differ in their functional properties (Ritter et al. 1999). Also, the L1 transposable element 1.4 kb upstream of the transcription start site might influence the CD163 promoter activity. CD163 is known to be involved in the innate immune response.

Matrix glycoprotein thrombospondin-1, Tsp1 (Galon et al., 2002) is a protein structurally related to matrix metalloproteinases (MMPs) and regulating their functions (Chen, 2000). Glucocorticoids have been shown to up-regulate Tsp1 expression.

The Toll-like receptors (TLRs) are type I transmembrane proteins that recognize microbes once they have breached physical barriers such as the skin or intestinal tract mucosa, and activate immune cell responses (Galon et al., 2002). TLRs recognize molecules that are broadly shared by pathogens but distinguishable from host molecules. TLR2 recognizes, for example lipoproteins, gram positive peptidoglycan and viral glycoproteins. TLR4 is a key component of the receptor for lipopolysaccharides (Beutler et al., 2006).

Expression of protein tyrosine kinase (TXK), also called resting lymphocyte kinase (RLK) is primarily detected in T cells, acting as a Th1 cell specific transcription factor (Takeba 2002; Wu et al., 2004) and in some myeloid cell lines. Activation of glucocorticoid receptor by dexamethasone treatment has been shown to induce expression of mitogen-activated protein kinase phospatase-1 (MKP-1) in breast cancer cell lines (Wu et al., 2004).

In one embodiment of the present invention the selected marker genes providing significant similarity or differences in expression levels in cells from patients and healthy volunteers, which cells have been cultivated in the presence of a steroid, an immunomodulatory oligonucleotide or a mixture thereof, are a CD163, a Tsp1, an IL1-R2, a TLR2, a TLR4, a MKP-1, a TXK marker gene.

In another embodiment of the invention the enhanced expression level of at least one marker gene in cells isolated from a sample of the patient and cultivated in the presence of a steroid, as compared to the expression level in the absence of the steroid, indicates that the patient would benefit from a steroid therapy. Preferably, the marker genes are CD163, Tsp1 and IL1-R2 genes.

In another embodiment of the present invention the enhanced expression level of at least one marker gene in cells isolated from a sample of the patient and cultivated in the presence of a steroid and an immunomodulatory oligonucleotide, as compared to the expression level in the absence of said steroid and immunomodulatory oligonucleotide, indicates that the patient would benefit from a combination therapy. Preferably, the marker gene is CD163, Tsp1 and IL1-R2 genes.

Herein the term "combination therapy" means providing steroid resistant patient in subsequent or simultaneous dosage forms or treatment regimen an effective amount of a steroid, an immunomodulatory oligonucleotide or mixtures thereof. One of the therapeutic agents may be provided before or after the other or both may be provide in a mixture as a single or mixed dose. An effective amount may vary between about 0.01 mg to about 2 mg/kg body weight and can be determined by the treating physician. The term combination therapy is preferably provided as a composition comprising an immunomodulatory oligonucleotide, with or without a steroid, with or without an alternative therapeutic agent and one or more pharmaceutically acceptable adjuvants or ingredients. The therapy may comprise varying courses of treating depending upon the disease and the condition of the patient, and may comprise a temporally spaced treatment regimen or modality, wherein the interval of dosing is speeded up or the intervals are delayed up to several months apart.

In a further embodiment of the invention, a significant difference in expression levels of at least one marker gene measured in isolated cells from a sample of a steroid resistant patient compared to corresponding sample isolated from a healthy person, cultivated in the presence of a steroid and an immunomodulatory oligonucleotide, indicates that a steroid resistant patient would benefit from being excluded from an corticosteroid therapy and being subjected to an alternative therapy comprising an immunomodulatory oligonucleotide. The alternative therapies in the present invention comprise an immunomodulatory oligonucleotide re-sensitization therapy either as monotherapy or in combination with, for example monoclonal antibodies, chemotherapy or radiation therapy. Preferably, the marker genes are TLR2, TLR4, MKP-1 and TXK.

Blood cells are preferred cells for the present invention. More preferably, the cell is a peripheral blood mononuclear cell (PMBC).

In one preferred embodiment of the present invention the inflammatory symptom includes acute or chronic asthma, emphysema, chronic obstructive pulmonary disease, ulcerative colitis, Crohn's disease, rheumatoid arthritis, and psoriasis.

In one embodiment of the invention the therapy is a combination therapy or an alternative therapy comprising and immunomodulatory oligonucleotide therapy. Preferably, the therapy is a steroid and an immunomodulatory oligonucleotide therapy. More preferably, the immunomodulatory oligonucleotide is the DNA-based Immunomodulatory Sequence IDX0150.

In one embodiment of the present invention, the steroid is a corticosteroid.

Preferably the corticosteroid is a dexamethasone, prednisolone or derivatives or mixtures thereof.

In one embodiment of the invention, the expression level of said marker gene is determined by nucleic acid amplification of said gene using gene specific primer pairs, and quantifying the amplification results. Preferably, the nucleic acid amplification is performed by a real time PCR and using gene specific primer pairs chosen from SEQ ID NO: 1-7.

The term "gene specific primer pairs" are designed to hybridize or anneal to opposing strands of the DNA encoding the marker gene of interest such that through PCR amplification, a defined region of the marker gene is produced. A "primer pair" thus refers to two primers, one having a forward designation and the other having a reverse designation relative to their respective orientations on a double-stranded DNA molecule, also called a sense and antisense sequence, such that under the PCR amplification conditions described in this invention, the forward primer anneals to and primes the amplification of the sense sequence and reverse primer anneals to and primes amplification of the antisense sequence. Primers can be selected for use in the amplification reaction on the basis of, having minimal complementarity with other primers in the reaction (to minimize the formation of primer dimers) and having Tm values with the range of reaction temperatures appropriate for the amplification method, preferably PCR. In addition, primers can be selected so as to anneal with specific regions of RNA template such that the resulting DNA amplification product ranges in size from 50 to 1000 base pairs, preferably from 50 to 300 base pairs in length and most preferably around 150 base pairs in length.

For example, in the real time PCR of the present invention, the specific primer pair may consist of the oligonucleotide of SEQ ID NO: 1 as the forward primer and the oligonucleotide of SEQ ID NO: 2 as the reverse primer.

Primers, typically from 10 to 100 nucleotides, preferably from 10 to 60 nucleotides in length, include naturally occurring or synthetically produced oligonucleotides capable of annealing to the target nucleic acids and acting as the point of initiation of nucleic acid synthesis under appropriate conditions, i.e., in the presence of nucleoside triphosphates, a polymerization agent, suitable temperature, pH and buffer. The principles for designing oligonucleotide primers, as well as performing the PCR and detection of the amplified DNA products are well known in the art.

The present invention relates also to a test kit for selecting a therapy for a steroid resistant patient presenting with inflammatory symptoms, wherein said test kit comprises specific primer pairs for enabling in vitro analysis of expression level of at least one marker gene and instructions for use.

Preferably, said specific primer pairs are selected from the group of SEQ ID NO: 1-14, or functionally equivalent primer pairs specific for the CD163, Tsp1, IL1-R2, TLR2, TLR4, MKP-1 and TXK marker genes. Preferred specific primer pairs are selected from the group of SEQ ID NO: 1-6, or functionally equivalent primer pairs specific for the CD163, Tsp1 and IL1-R2 marker genes. Particularly preferred specific primer pairs are SEQ ID NO: 1 and SEQ ID NO: 2, or functionally equivalent primer pairs specific for the CD163 gene.

The term "functionally equivalent" means another primer, which need not be any of the listed primers, but has a sequence, which is complementary to a specific strand of the marker gene, and enables hybridization or amplification reactions.

According to one embodiment of the invention, the kit further comprises means for cultivating cells. Preferably, the kit comprises an agent for sensitizing the cells. Such an agent may be a steroid, an immunomodulatory oligonucleotide or a mixture thereof.

In another embodiment of the invention, the kit further comprises means for carrying out hybridization or amplification assay.

The present invention also relates to the use of the method as described previously for determining steroid responsiveness of a steroid resistant patient.

The present invention also relates to the use of the method as described previously for identifying a steroid resistant patient, who would benefit from an immunomodulatory oligonucleotide therapy.

The present invention further relates to the use the method as described previously for screening whether an immunomodulatory compound enhances steroid responsiveness of a steroid resistant patient.

The present invention further relates to the use of CD163, Tsp1, IL1-R2, TLR2, TLR4, MKP-1 and TXK genes for preparing a reagent for in vitro identification of steroid patients, which would benefit from corticosteroid therapy.

The present invention further relates to the use of CD163, Tsp1, IL1-R2, TLR2, TLR4, MKP-1 and TXK genes for preparing a reagent for in vitro identification of steroid patients, which would benefit from a combination therapy comprising a steroid therapy and an immunomodulatory oligonucleotide therapy.

The present invention also relates to the use of TLR2, TLR4, MPK-1 and TXK genes for preparing a reagent for in vitro identification of steroid patients, which would benefit from being excluded from steroid therapy.

The present invention further relates to the use of TLR2, TLR4, MPK-1 and TXK genes for preparing a reagent for in vitro identification of steroid patients, which would benefit from being subjected to an alternative therapy comprising the administration of an immunomodulatory oligonucleotide.

The present invention also relates to the use of CD163, Tsp1, IL1-R2, TLR2, TLR4, MKP-1 and TXK genes for preparing a reagent for in vitro identification of steroid patients, which would benefit from steroid therapy or a combination therapy and those which would benefit from being excluded from steroid therapy, wherein the reagent is a primer pair specific for said genes.

The present invention also relates to the use of CD163, Tsp1, IL1-R2, TLR2, TLR4, MKP-1 and TXK genes for preparing a reagent for in vitro identification of steroid patients, which would benefit from steroid therapy or a combination therapy and those which would benefit from being excluded from steroid therapy, wherein the reagent is an oligonucleotide probe, which is complementary to a specific region of said genes and capable of hybridizing or annealing with said genes.

An advantage of the embodiments of the invention is that it will now be possible to objectively assess steroid resistance, both qualitatively and quantitatively. It also becomes possible to identify not only this patient group, but also to distinguish between sub-groups thereof, for example patients likely to respond to resensitization, but who are slow-responders or require repeated treatments.

The invention is a step towards more individualized therapy, in that the condition of an individual patient can be accurately determined, as well as in that the response of the patient can be predicted, and the most suitable therapy chosen. Further advantages will be evident to a skilled person upon study of the description, examples and claims.

The following examples firstly present the test materials, including therapeutic compounds and cells used in the study as well the conditions to study expression profiles of selected genes and methods to quantify the expression levels. The following examples present the evaluation of results and selection of marker genes to determine those capable for indicating re-sensitization or resistance to a given therapy.

The latter examples are examples of screening other potential marker genes linked to other cell types from an asthma patient OR from cells of patients with other inflammation diseases, such as rheumatoid arthritis, ulcerative colitis and Crohn's disease, and selection of marker genes useful in predicting steroid responsiveness in these diseases as well as determining the response of cells to a corticosteroid, an immunomodulatory oligonucleotide or a mixture thereof. The correlation between the results obtained in the in vitro method of the present invention and in vivo will be verified in pre-clinical and possibly also clinical trials scheduled to be performed during the priority year.

EXAMPLES

Example 1

Materials and Methods
Test articles

In the invention the DNA-based immunomodulatory oligonucleotide IDX0150, containing a CpG motif (also known as IDX0150; Kappaproct®, InDex Pharmaceuticals AB, Stockholm, Sweden) was used to study stimulation of the defined genes in human peripheral blood mononuclear cells (PMBC). Lyophilized IDX0150 was weighed and dissolved in 1×PBS pH 7,4 (Gibco) at room temperature. The stock concentration was adjusted by aid of UV spectrophotometry (SmartSpec™ 3000, BIORAD) to 95% accuracy. The IDX0150 stock solution was stored at −20° C. For the stimulation experiment, one portion of the stock solution was diluted further, in order to obtain one low and one high concentration of stock solution (25 µM and 100 µM, final concentration, respectively). The concentration was determined in the same manner, measuring optical density (OD) using a spectrophotometer as mentioned above.

The corticosteroid dexamethasone (Dex) used in the experiments was purchased from Sigma (Cat. No. D-8893) as a powder and dissolved to stock concentration of 20 mg/ml in a RPMI medium (Gibco/Sigma), a medium first developed at Roswell Park Memorial Institute (RPMI) utilizing a bicarbonate buffering system and alterations in the amounts of amino acids and vitamins. Dexamethasone stock solution was stored at 4° C.

Seven candidate genes for developing an in vitro, RT-PCR based assay of the invention were selected (Table 1). These genes include IL1-R2, one member of macrophage scavenger receptor family (CD163), a matrix glycoprotein thrombospondin-1, two members of interleukin 1 signaling pathway (TLR2 and TLR4) and two enzymes (MKP-1 and TXK).

TABLE 1

Genes related to human PBMC steroid response

| No. | Gene | Name/Function | Reference |
|---|---|---|---|
| 1 | CD163 | Hemoglobin scavenger receptor | Galon et al., 2002 |
| 2 | Tsp1 | Thrombospondin-1, matrix glycoprotein | Galon et al., 2002 |
| 3 | IL1-R2 | Interleukin 1 receptor, type II | Galon et al., 2002 |
| 4 | TXK | Tyrosine kinase | Wu et al., 2004 |
| 5 | TLR2 | Toll-like receptor, signal transduction | Galon et al., 2002 |
| 6 | TLR4 | Toll-like receptor, signal transduction | Galon et al., 2002 |
| 7 | MKP-1 | Tyrosine phosphatase | Wu et al., 2004 |

The PCR primer oligonucleotides specific for the candidate genes were designed by using 7500 System Applied Biosystems software Primer Express (v.3). Primer oligonucleotides were custom ordered from MWG Biotech (Edersberg, Germany). The primers were dissolved in sterile deionised water (Gibco) at room temperature. All primer oligonucleotides were stored at −20° C. The sequences of the PCR primer oligonucleotides used are listed in Table 2.

TABLE 2

PCR primer oligonucleotides

| Primer | Sequence ID | Sequence (5'-3') |
|---|---|---|
| CD163 forward | SEQ ID NO: 1 | GCTGCAGTGAATTGCACAGATAT |
| CD163 reverse | SEQ ID NO: 2 | CGGGATGAGCGACCTGTT |
| Tsp1 forward | SEQ ID NO: 3 | CATCCGCAAAGTGACTGAAGAG |
| Tsp1 reverse | SEQ ID NO: 4 | GTACTGAACTCCGTTGTGATAGCATAG |
| IL1-R2 forward | SEQ ID NO: 5 | TCACTAGGAGTATTGAGCTACGCATC |
| IL1-R2 reverse | SEQ ID NO: 6 | ATTGTCAGTCTTGACCCCAGAGA |
| TXK forward | SEQ ID NO: 7 | CAATGCAGCCGGTCTCATG |
| TXK reverse | SEQ ID NO: 8 | TCTCCCACTTTTCGTAGCTAAACC |
| TLR2 forward | SEQ ID NO: 9 | AGGAGCTCTTAGTGACCAAGTGAAG |
| TLR2 reverse | SEQ ID NO: 10 | CCCACACCATCCACAAAGTATG |
| TLR4 forward | SEQ ID NO: 11 | CCCTGCGTGGAGGTGGTT |
| TLR4 reverse | SEQ ID NO: 12 | ATATGCCCCATCTTCAATTGTCT |
| MKP-1 forward | SEQ ID NO: 13 | GGAGGATACGAAGCGTTTTCG |
| MKP-1 reverse | SEQ ID NO: 14 | ACCGGGCCACCCTGAT |

Biological Systems
Cell Preparation

Peripheral blood mononuclear cells (PMBC) were isolated from blood samples of seven steroid resistant asthma or ulcerative colitis patients and ten healthy volunteers by density gradient centrifugation using Ficoll-Paque Plus (Pharmacia Biotech), washed three times in buffered saline solution (PBS), and resuspended in complete RPMI 1640 (Sigma/Gibco) containing 15% heat inactivated fetal bovine serum (FCS) (Gibco, Life Technologies), 100 U/ml penicillin, 100 µg/ml streptomycin (Life Technologies), 2 mM L-glutamine (Sigma), gentamycin 25 ug/ml (Sigma) and 5 mM Hepes (Gibco, Life Technologies). Cells were counted using 0.4% Trypan blue solution (Sigma Aldrich). On average the yield of PBMC was in range of 60-120×10$^6$ cells per donor sample.

Techniques

In Vitro Stimulation of PBMC

PBMCs, prepared as described previously, were resuspended in RPMIc containing 5% of FBS (Gibco, Life Technologies) and seeded into a 96-well flat bottomed cell culture plate (Falcon) at a cell density of 0,5×10$^6$ cells per well. Immediately after plating, cells were stimulated with IDX0150 (25 µM or 100 µM) in the presence or absence of corticosteroid Dex ($10^{-10}$, $10^{-8}$ or $10^{-6}$ M). During the treatment, cells were incubated in a humified SteriCycle $CO_2$ cell culture incubator (ThermoForma) at 5% carbon dioxide ($CO_2$), 37° C. for 48 hrs. After the incubation period the supernatant was aspirated and the cells covered by 50 µl/well of RLT-lysis buffer (Qiagen) containing 1.0% of β-mercaptoethanol. The culture plates with the PBMC were saved at −20° C. until RNA isolation procedure.

Total RNA Isolation from Stimulated PBMC 96-well plates, prepared as described above, were removed from −20° C. and allowed to thaw at room temperature. After thawing, PBMC were resuspended in 50 µl/well of RLT lysis buffer (Qiagen) containing 1.0% of β-mercaptoethanol. RNA isolation was performed using RNeasy RNA isolation kit (Qiagen) according to the instructions of the manufacturer. RNA was eluted in 40 µl of RNase-free water and 5 µl of the RNA eluate was used to determine the RNA concentration by spectrophotometry (SmartSpec™ 3000, BIO-RAD). Quality of RNA was checked by gel electrophoresis on a 1% agarose (Sigma) gel buffered with 1×TAE and containing ethidium bromide to visualize RNA.

Conventional cDNA Synthesis

For the first strand cDNA synthesis 0.3-1.0 µg of total PBMC RNA was subjected to conventional reverse transcription with the polymerase chain reaction (RT-PCR) using d(T)$_{20}$ oligonucleotide as a primer. Double stranded cDNA was synthetized by PCR using PCR primer oligonucleotides (Table 2) specific for the selected nucleotide sequences (Table 1). cDNA stock solutions were diluted in adequate volume of sterile deionised water (Gibco). cDNA samples were analyzed by gel electrophoresis on 1% agarose (Sigma) gel buffered with 1×TAE and containing ethidium bromide to confirm expected length of the synthetised PCR products.

Aliquotes of the RT-PCR reaction samples were sequenced at MWG Biotech (Edersberg, Sverige) and the resulted DNA sequences were verified by NCBI Blast bioinformatics analysis.

Real Time PCR Analysis of the PBMC cDNA

Real-time PCR with PBMC cDNA was performed in triplicates for each sample-treatment/gene combination for considered genes and in duplicate for a housekeeper gene (γ-actin). Double stranded cDNA was synthetized by real time PCR using PCR primer oligonucleotides (Table 2) specific for the selected nucleotide sequences (Table 1). Real-time PCR data for individual Cycle threshold (deltaCt) and Relative Quantitation (RQ) values were calculated and analysed with 7500 System SDS Software according to the instructions of the supplier (Applied Biosystems). The individual values were exported to Excel and analysed statistically. Basal level of gene expression in non-treated samples was determined in Excel by calculation of RQ value from individual deltaCt values.

For each particular gene all average RQ values were normalised against average RQ value of basal expression of this gene. To evaluate individual values distribution the average deviations of values range were calculated. The normalised average RQ values with indication of average deviation of values range were plotted in Excel. The distributions of individual expression values were plotted using GraphPad Prism version 4.03 for Windows, GraphPad Software, San Diego Calif. USA, www.graphpad.com.

Evaluation of Gene Expression of PBMC Upon Stimulation with IDX0150

Seven selected genes were analyzed for gene expression in a PBMC culture experiment as described previously. For each gene/patient pair PBMC culture was split in 6 aliquote samples for treatment with a CpG containing oligonucleotide IDX0150 or corticosteroid Dex or IDX0150/Dex in combination. IDX0150 was used at final concentrations of 25 and 100 µM and Dex was added into the cell growth medium at final concentrations of $10^{-10}$, $10^{-8}$ or $10^{-6}$ M. Cells were cultivated 48 hours as described previously.

The results of the gene expression are presented in Examples 2-8.

Example 2

Evaluation of CD163 Gene Expression of PBMC Upon Stimulation with IDX0150

PBMC culture experiment setup performed was as described in Example 1. The average values of expression level of CD163 gene are presented in FIGS. 1 and 4. Deviation bars show range of expression level values in groups of healthy volunteers (HV) and steroid resistant asthma or ulcerative colitis patients (SR). The average expression level value was normalized against the basal expression level value as described in Example 1.

Figure 4:
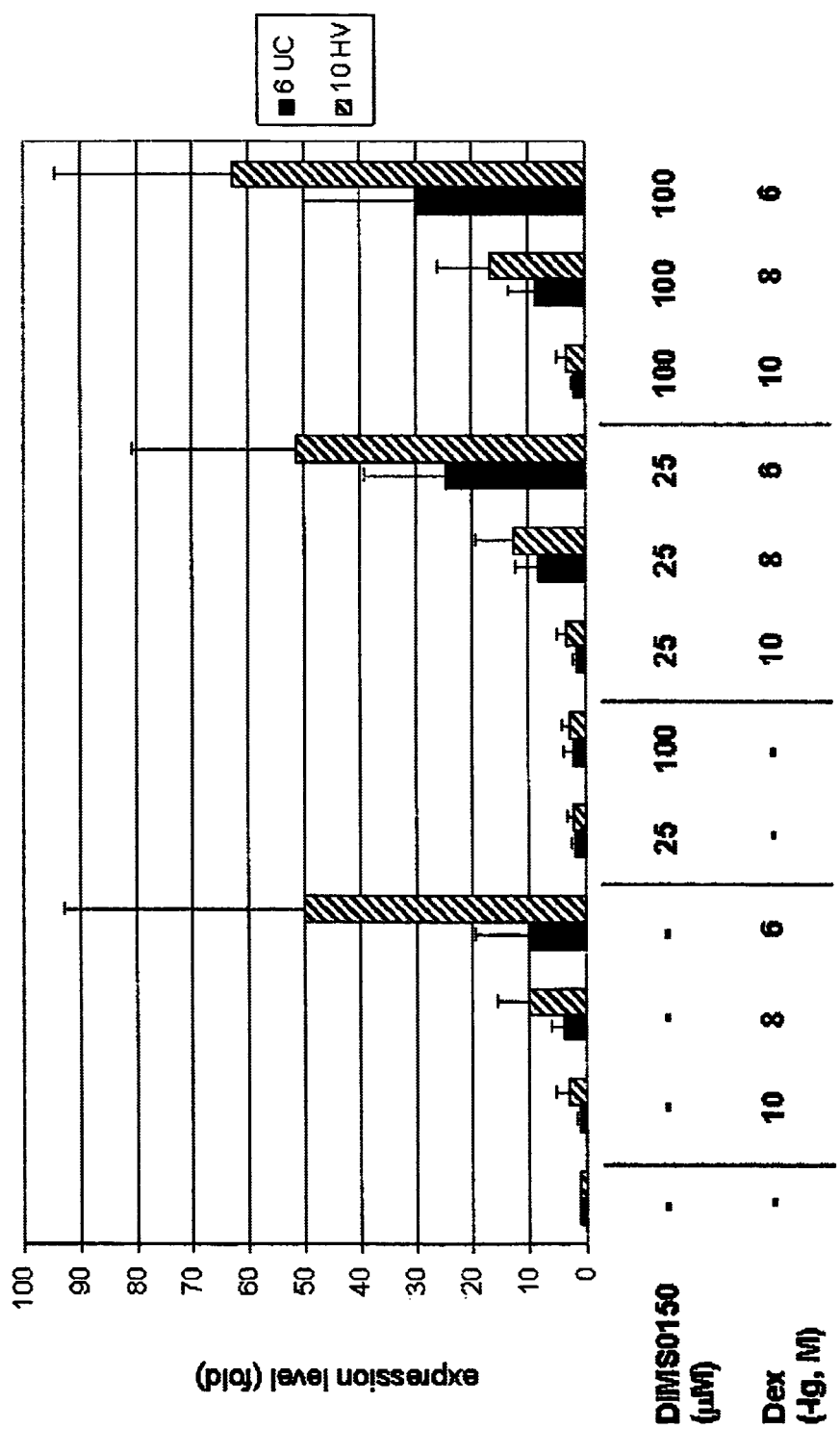
FIG. 4 depicts the average value of expression level of CD163 gene in peripheral blood mononuclear cells (PBMC) in response to 48 hrs stimulation with the immunomodulatory oligonucleotide IDX0150 alone, dexamethasone (Dex) alone, or IDX0150 and Dex in combination as quantified by real-time PCR. PBMC were isolated from blood samples of ten (n=10) healthy volunteers (HV) and seven (n=7) steroid resistant ulcerative colitis patients (SR). Cells were incubated in a basal medium or in a basal medium with increasing concentrations of IDX0150 (25 µM or 100 µM) in the presence or absence of Dex at increasing concentrations ($10^{-10}$, $10^{-8}$ or $10^{-6}$ M) as described in Example 1. After incubation, the total RNA was isolated from PBMCs and used for first strand cDNA synthesis. Real-time PCR reactions with PBMC cDNA were performed in triplicates for each sample/treatment combination and in duplicates for a housekeeper gene (γ-actin). Each bar of the histogram represents the average expression level value, normalized by basal expression level value as described in Example 1. The error-bars indicate the deviation range of the values of expression levels in different blood donors.
Figure 5:
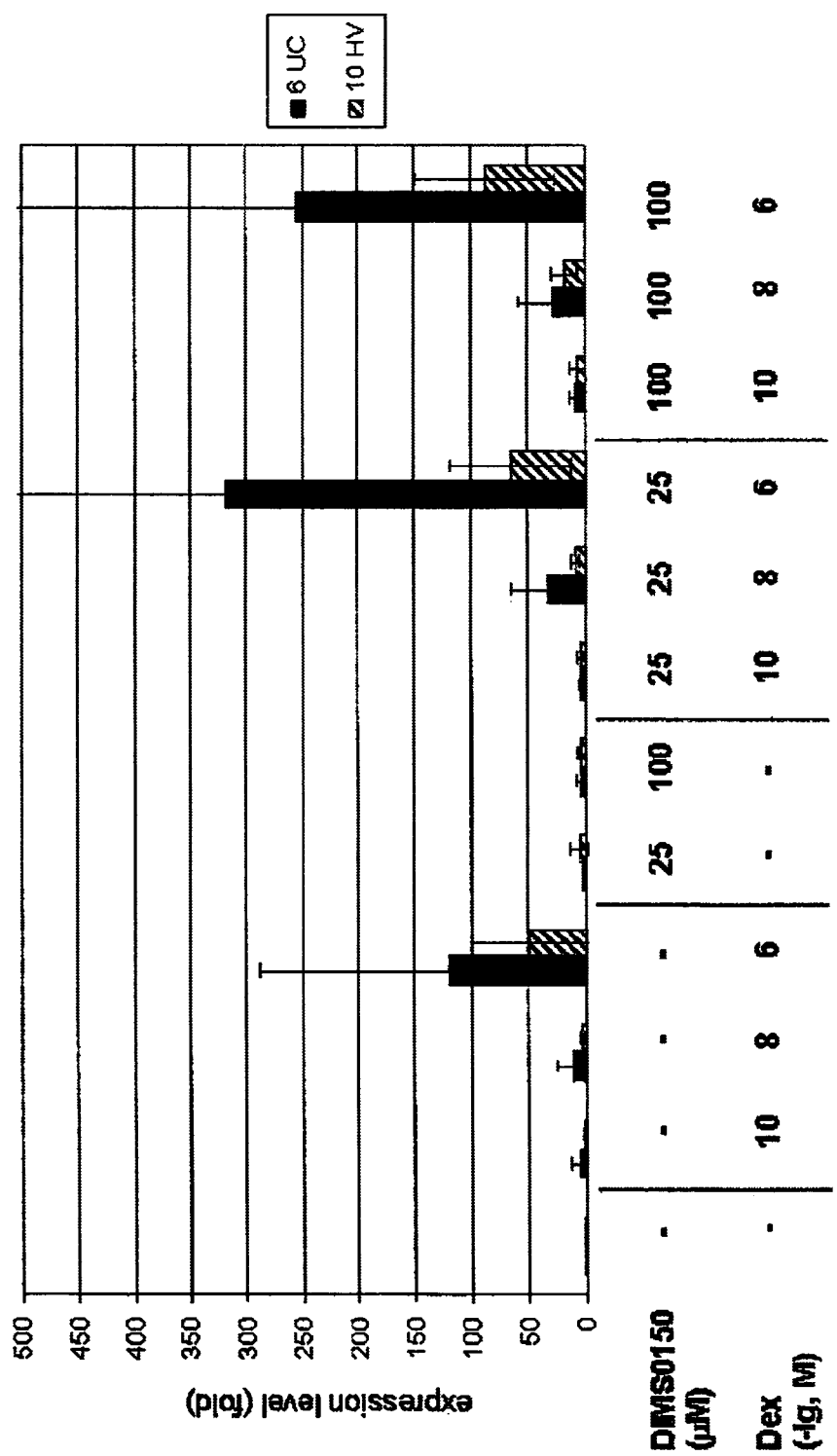
FIG. 5 depicts the average value of expression level of Tsp1 gene in PBMC in response to 48 hrs stimulation with IDX0150 alone, Dex alone, or IDX0150 and Dex combination as quantified by real-time PCR. The experimental conditions and data handling were as described in FIG. 4 and Example 1.
Figure 6:
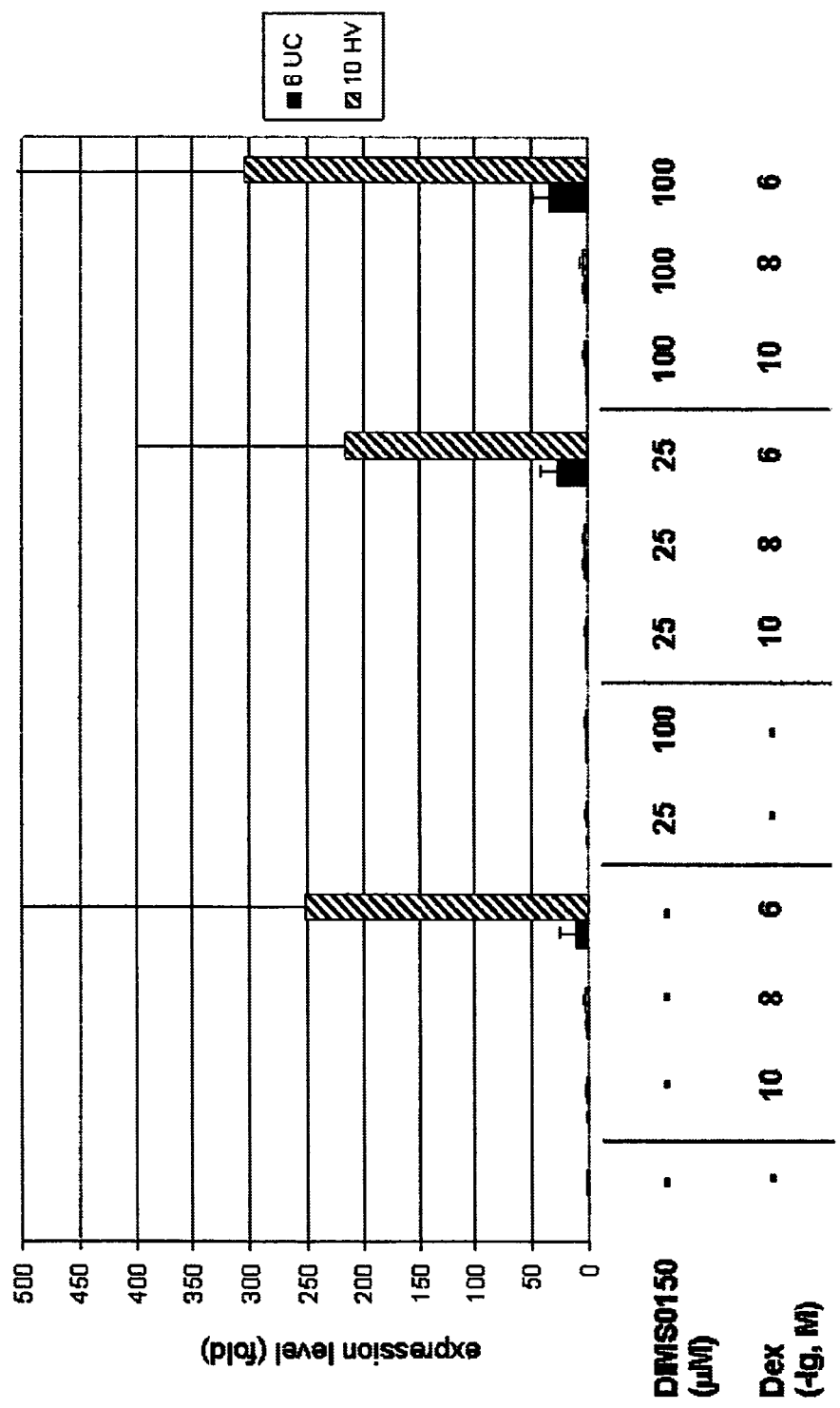
FIG. 6 depicts the average value of expression level of IL1-R2 gene in PBMC in response to 48 hrs stimulation with IDX0150 alone, Dex alone, or IDX0150 and Dex combination as quantified by real-time PCR. The experimental conditions and data handling were as described in FIG. 4 and Example 1.
Figure 7:
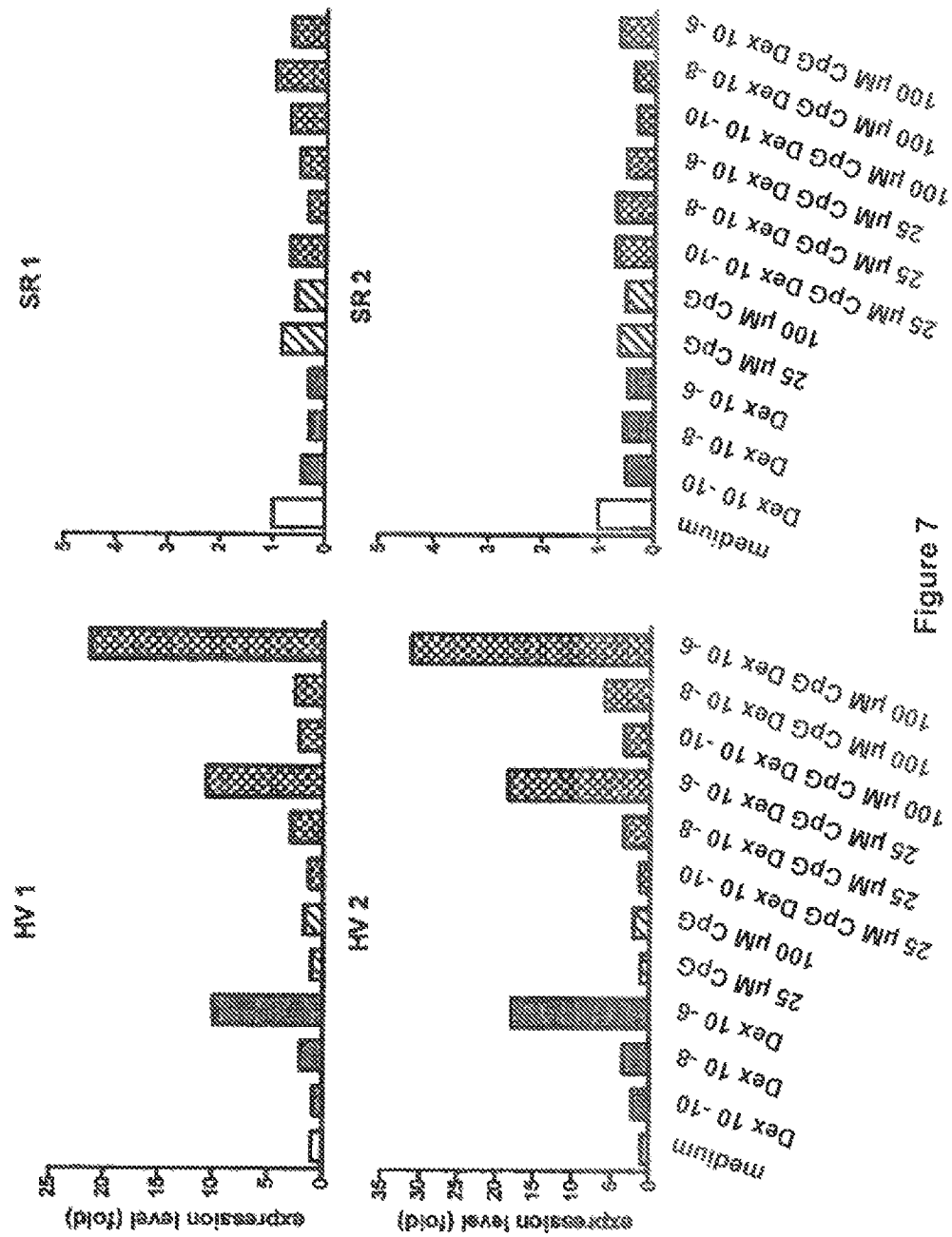
FIG. 7 depicts the average value of expression level of TLR2 gene in PBMC in response to 48 hrs stimulation with IDX0150 alone, Dex alone, or IDX0150 and Dex combination as quantified by real-time PCR. The experimental conditions and data handling were as described in FIG. 1 and Example 1.
Figure 8:
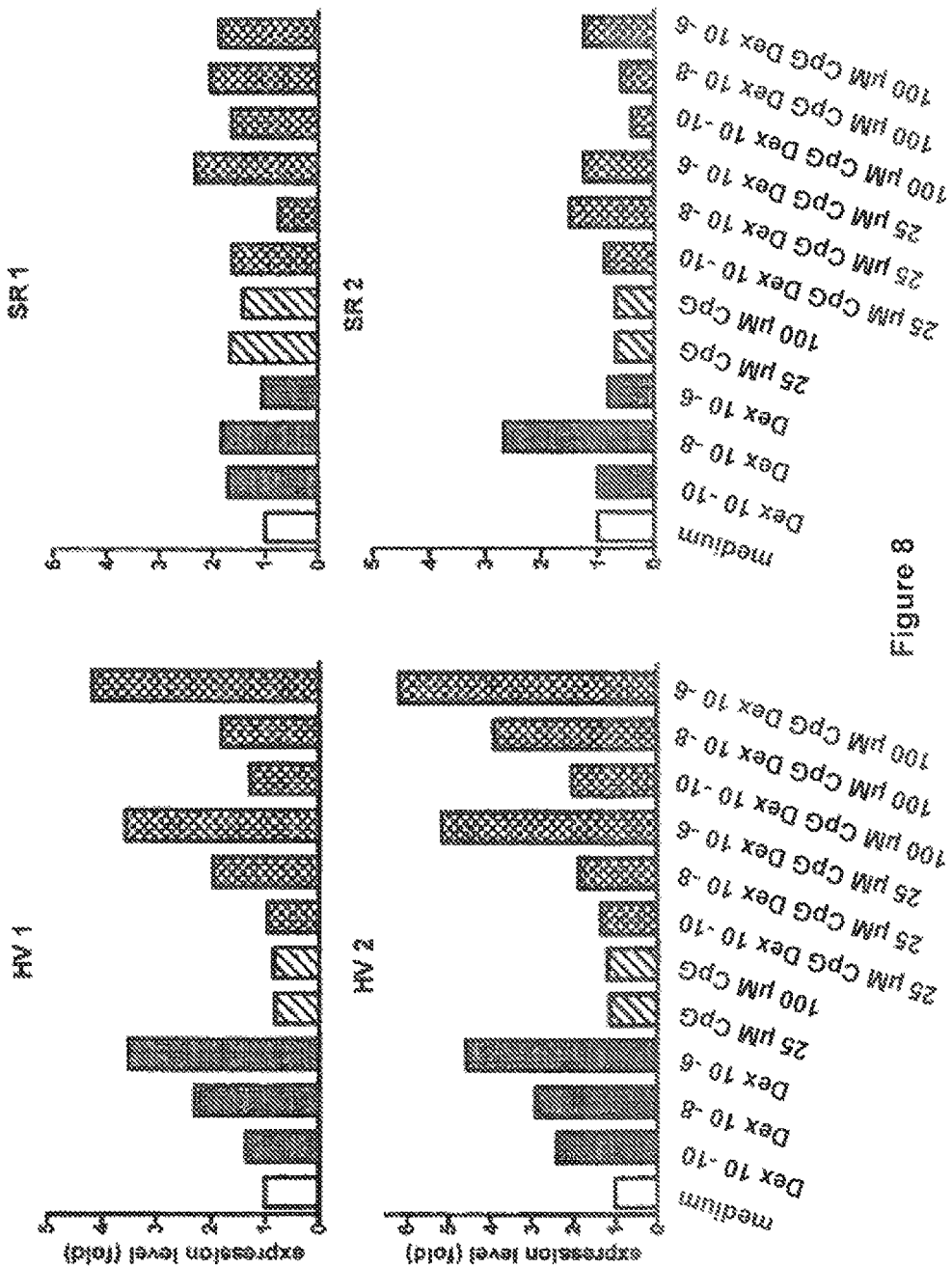
FIG. 8 depicts the average value of expression level of TLR4 gene in PBMC in response to 48 hrs stimulation with IDX0150 alone, Dex alone, or IDX0150 and Dex combination as quantified by real-time PCR. The experimental conditions and data handling were as described in FIG. 1 and Example 1.
Figure 9:
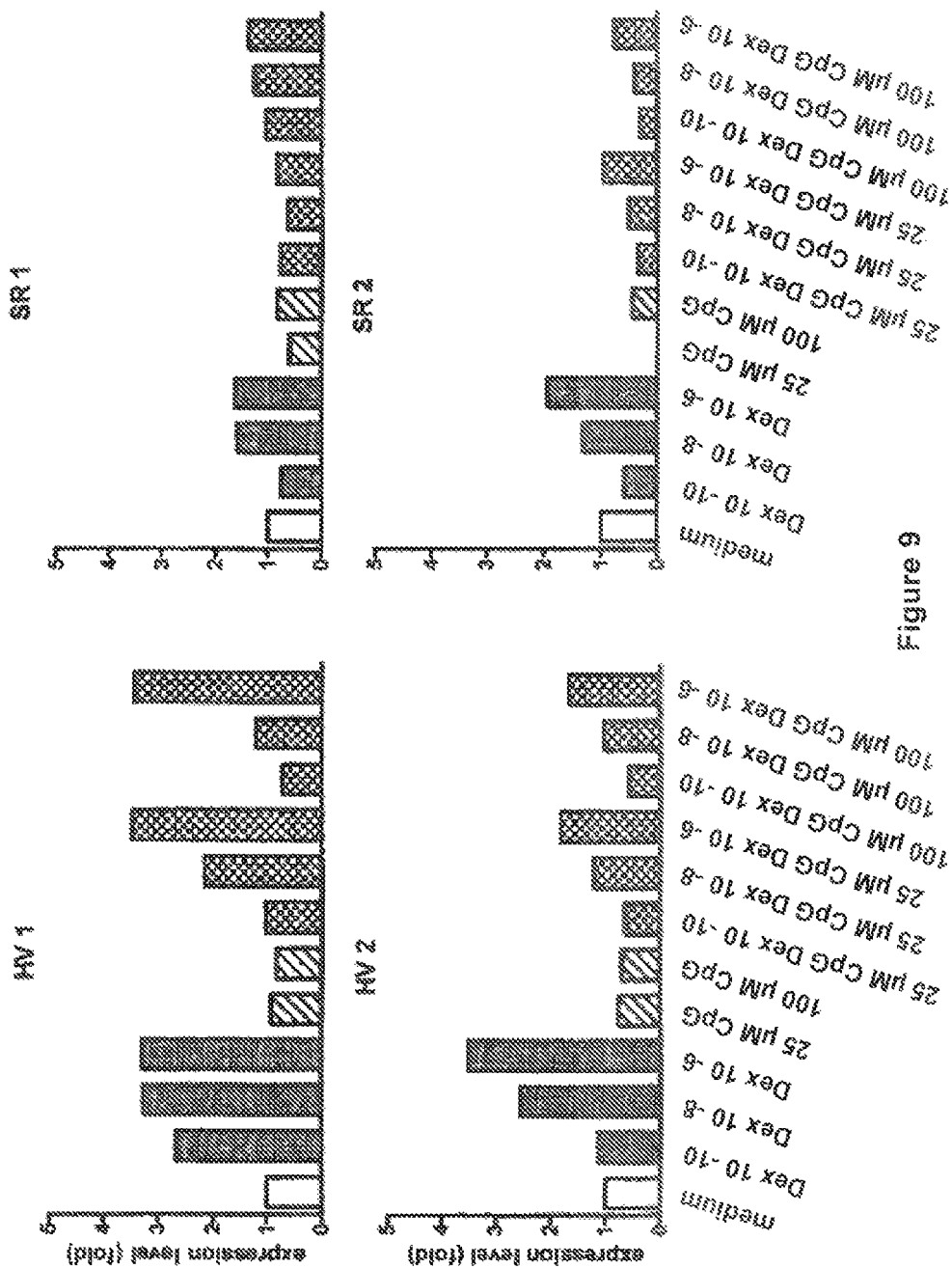
FIG. 9 depicts the average value of expression level of TXK gene in PBMC in response to 48 hrs stimulation with IDX0150 alone, Dex alone, or IDX0150 and Dex combination as quantified by real-time PCR. The experimental conditions and data handling were as described in FIG. 1 and Example 1.
Figure 10:
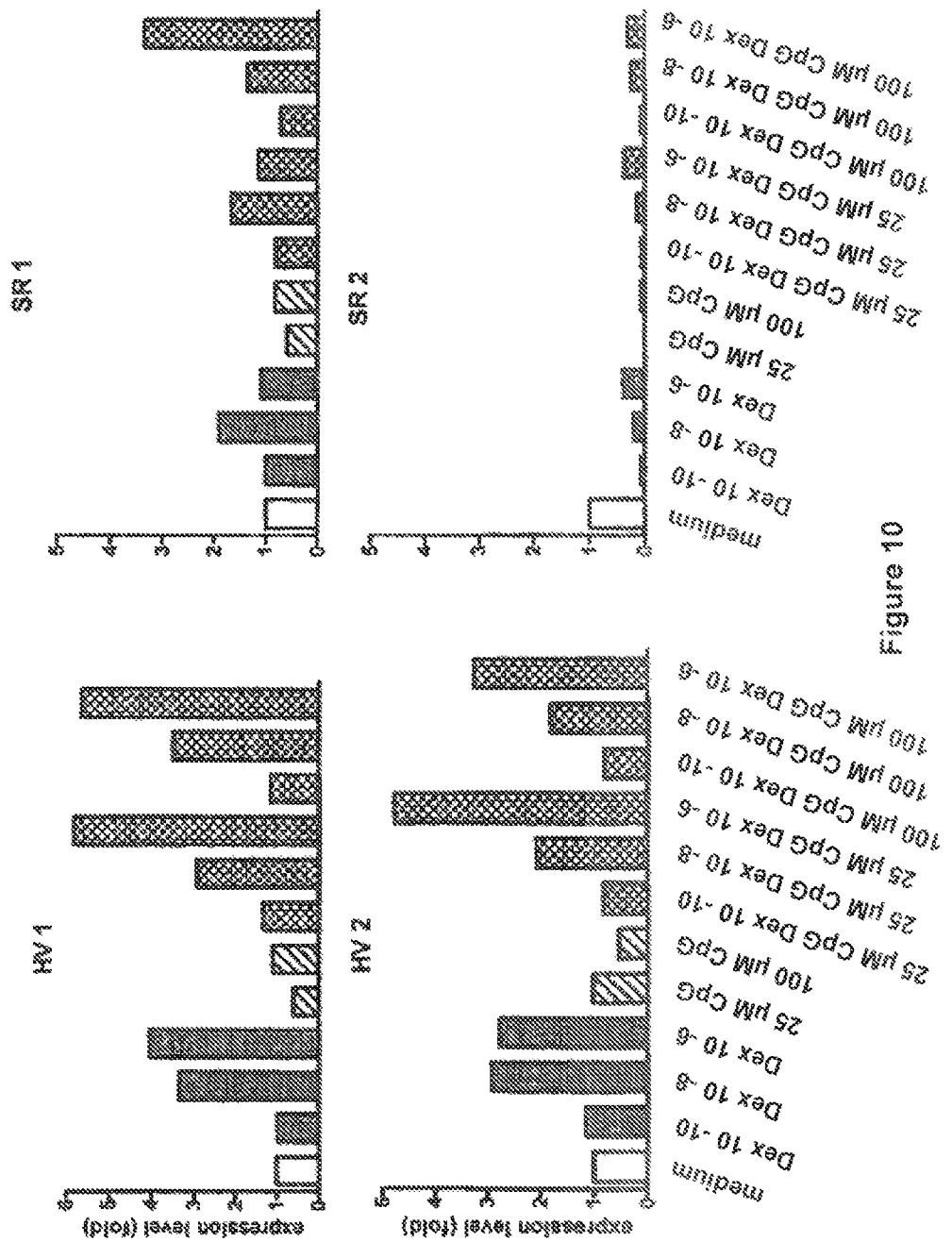
FIG. 10 depicts the average value of expression level of MKP1 gene in PBMC in response to 48 hrs stimulation with IDX0150 alone, Dex alone, or IDX0150 and Dex combination as quantified by real-time PCR. The experimental conditions and data handling were as described in FIG. 1 and Example 1.

Scavenger receptors are known to be involved in the innate immune response. CD163 expression has been shown to be up-regulated by anti-inflammatory mediators and corticosteroids (Buechler, 2000; Galon, 2002). The present study confirmed that CD163 expression was up-regulated by the corticosteroid dexamethasone (Dex) in a dose dependent manner both in the PBMC of healthy volunteers (HV) and steroid resistant patients (SR) and showed for the first time that this up-regulation was strongly increased by co-treatment with IDX0150 in both groups (FIGS. 1 and 4). The enhancing effect was even more pronounced in the samples of steroid resistant asthma and ulcerative colitis patients (SR). The observation provides evidence for a steroid "enhancing" effect of IDX0150 in both test groups.

Example 3

Evaluation of Tsp1 and IL1-RL2 Gene Expression of PBMC Upon Stimulation with IDX0150

Thrombospondins are structurally related to matrix metalloproteinases (MMPs) and regulate their functions (Chen, 2000). The expression of Tsp1 has been shown to be up-regulated by glucocorticoids (Galon, 2002). Also IL1-R2, an anti-inflammatory decoy receptor limiting the deleterious effects of interleukin 1 (IL-1), is among the genes strongly up-regulated by glucocorticoids (Re, 1994; Galon, 2002).

PBMC culture experiment setup was performed as described previously (see Example 1).

Figure 2:
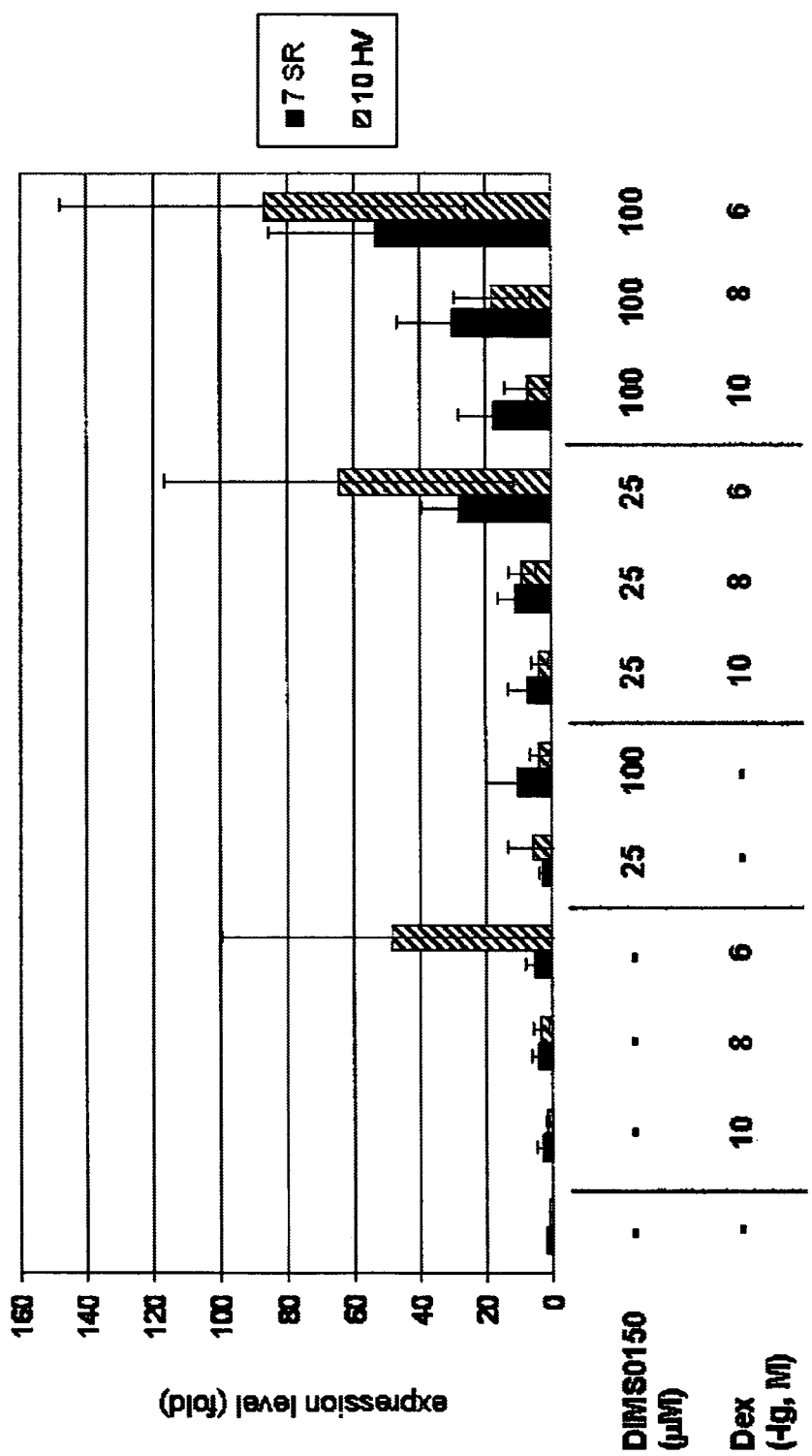
FIG. 2 depicts the average value of expression level of Tsp1 gene in PBMC in response to 48 hrs stimulation with IDX0150 alone, Dex alone, or IDX0150 and Dex combination as quantified by real-time PCR. The experimental conditions and data handling were as described in FIG. 1 and Example 1.
Figure 3:
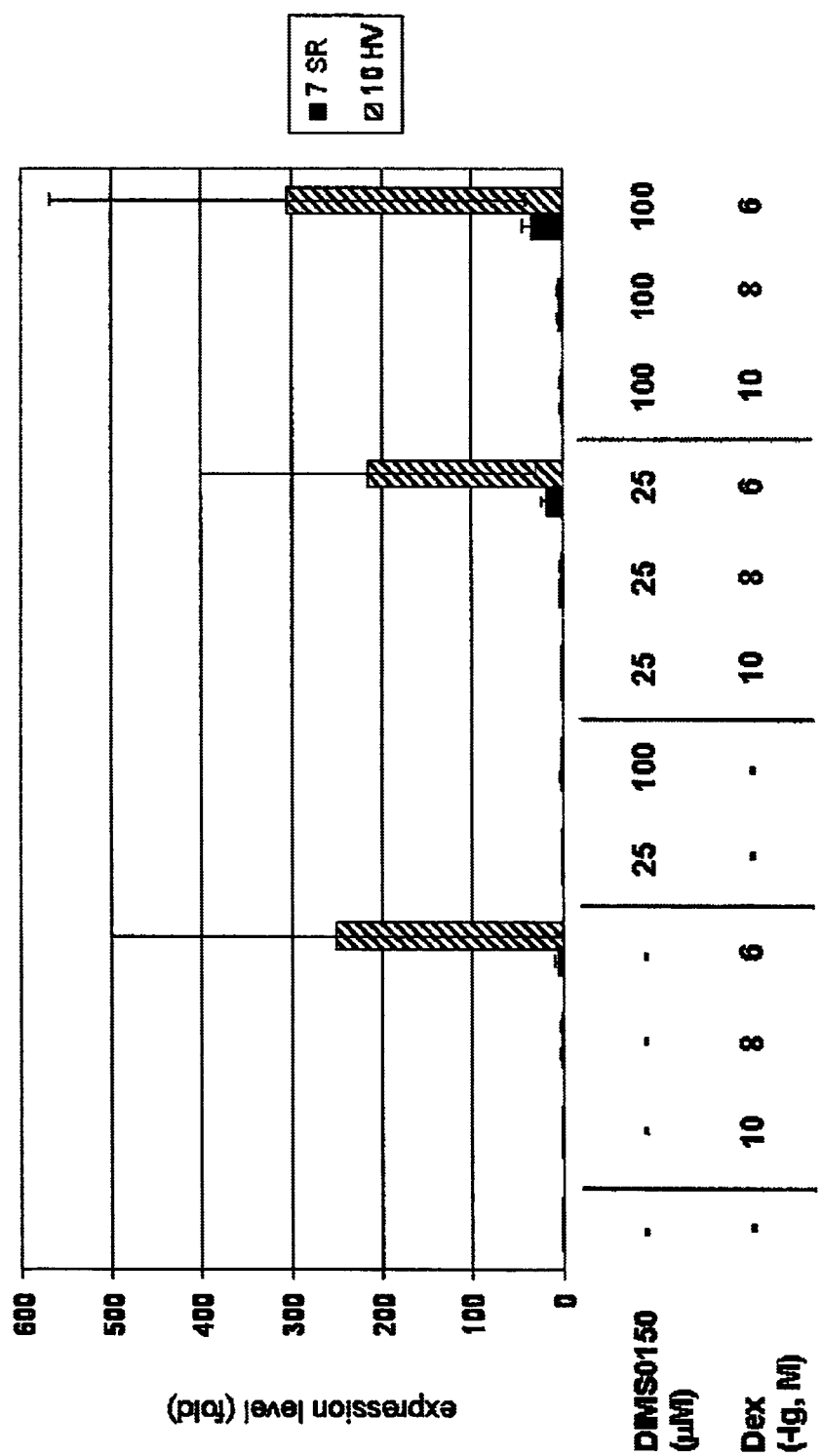
FIG. 3 depicts the average value of expression level of IL1-R2 gene in PBMC in response to 48 hrs stimulation with IDX0150 alone, Dex alone, or IDX0150 and Dex combination as quantified by real-time PCR. The experimental conditions and data handling were as described in FIG. 1 and Example 1.

The average values of expression levels of Tsp1 and IL1-R2 genes are presented in FIGS. 2, 3 (asthma) and 5, 6 (ulcerative colitis), respectively. Approximately 3-5 fold induction of Tsp1 and IL1-R2 was demonstrated by $10^{-6}$ M Dex. The results showed for the first time that Tsp1 and IL1-R2 up-regulation could be strongly increased in a dose dependent manner by co-treatment with IDX0150. The effect was even more pronounced in the samples of steroid resistant asthma and ulcerative colitis patients (SR). The observation provides evidence for a steroid "enhancing" effect of IDX0150 in both test groups.

Example 4

Evaluation of TLR2, TLR4, MKP-1 and TXK Gene Expression of PBMC Upon Stimulation with IDX0150

PBMC culture experiment setup was performed as described previously (see Example 1). The average values of expression levels of TLR2, TLR4, MKP-1 and TXK genes are presented in FIGS. 7, 8, 9 and 10, respectively.

TLR2, TLR4, MPK-1 and TXK genes showed different expression levels in PBMC material of healthy volunteers (HV) in comparison with steroid resistant asthma patients (SR), when treated with only Dex and in combination of IDX0150 and Dex (FIGS. 7-10).

The observation supports the use of these genes as putative markers for resistance of asthma patients to corticosteroid treatment when compared to the expression of these genes in healthy persons.

Example 5

Human Pilot Study

Clinical studies are in progress with the primary objective to explore the clinical efficacy of the combination therapy comprising a DNA-based immunomodulatory oligonucleotide IDX0150 (Kappaproct®, InDex Pharmaceuticals AB) and a corticosteroid dexamethasone, and particularly to explore the correlation between an in vitro method according to an embodiment of the present invention. The study will also test the clinical efficacy of the treatment selected based on said in vitro method. The test group consists of ulcerative colitis patients, which in the in vitro method have been shown to be responsive to said combination therapy, i.e. PBMC cells obtained from these patients showed enhanced expression of selected marker genes in the presence of a steroid and an immunomodulatory oligonucleotide. The clinical efficacy is determined by endoscopic and clinical remission/improvement rates, histological improvement and changes in clinical laboratory parameters.

The study is placebo controlled; double blinded single dose and considered patients that were unresponsive to corticosteroids or corticosteroid dependent who were on concomitant steroid therapies.

The dose level used is 3 mg and 30 mg given as a single rectal administration.

Although particular embodiments have been disclosed herein in detail, this has been done by way of example for purposes of illustration only, and is not intended to be limiting with respect to the scope of the appended claims that follow. In particular, it is contemplated by the inventor that various substitutions, alterations, and modifications may be made to the invention without departing from the spirit and scope of the invention as defined by the claims.

References

Beutler B, Jiang Z, Georgel P, Crozat K, Croker B, Rutschmann S, Du X, Hoebe K. 2006. Genetic analysis of host resistance: Toll-like receptor signaling and immuninty at large. Ann. Rev. Immunol. 24: 353-389.

Buechler C, Ritter M, Orso E, Langmann T, Klucken J, Schmitz G. 2000. Regulation of scavenger receptor CD163 expression in human mononuclear cells and macrophages by pro-and antiinflammatory stimuli. J. Leukoc. Biol. 67: 97-103.

Chen H, Herndon M E, Lawler J. 2000. The cell biology of thrombospondin-1. Matrix Biol. 19: 597-614.

Chrousos G P, Vingerhoeds A, Brandon D. 1982. Primary cortisol resistance in man. A glucocorticoid receptor-mediated disease. J. Clin. Invest. 69(6): 1261-1269.

Chrousos G P, Detera-Wadleigh S D, Karl M. 1993. Syndromes of glucocorticoid resistance. Ann. Intern. Med. 119(11): 1113-1124.

Clark J K, Schrader W T, O'Malley B W. 1992. Mechanism of steroid hormones. 1992. In: J D Wilson, D W Foster, eds. Williams Textbook of Endocrinology. WB Saunders Co., Philadelphia, Pa., pp. 35-90.

Cole T J, Blendy J A, Monaghan A P. 1995. Targeted disruption of the glucocorticoid receptor gene blocks adrenergic chromaffin cell development and severely retards lung maturation. Genes. Dev. 9(13): 1608-1621.

Cowdery J S, Chace J H, Yi A K, Krieg A M. 1996. Bacterial DNA induces NK cells to produce IFN-gamma in vivo and increases the toxicity of lipopolysaccharides. J. Immunol. 156(12): 4570-4575.

Galon J, Franchimont D, Hiroi N, Frey G, Boettner A, Ehrhart-Bornstein M., O'Shea J J, Chrousos G P, Bornstein S R. 2002. Gene profiling reveals unknown enhancing and suppressive actions of glucocorticoids on immune cells. FASEB J. 16(1): 61-71.

Gisbert J P et al., 2008. Crohnology: A tale of time and times and inflammatory bowel diseases. World J Gastroenterol. 14(36): 5504-7.

Iho S, Yamamoto T, Takahashi T, Yamamoto S. 1999. Oligodeoxynucleotides containing palindrome sequences with internal 5'CpG-3' act directly on human NK and activated T cells to induce IFN-gamma production in vitro. J. Immunol. 163(7): 3642-3652.

Jakob T, Walker P S, Krieg A M, Udey M C, Vogel J C. 1998. Activation of cutaneous dendritic cells by CpG-containing oligodeoxynucleotides: a role for dendritic cells in the augmentation of TH1 responses by immunostimulatory DNA. J. Immunol. 161(6): 3042-3049.

Kline J N. 2000. Effects of CpG DNA on Th1/Th2 balance in asthma. Curr. Top. Microbiol. Immunol. 247: 211-225.

Krieg A. 1996. Lymphocyte activation by CpG dinucleotide motifs in prokaryotic DNA. Trends Microbiol. 4(2): 73-76.

Krieg A. 1998. Leukocyte stimulation by oligodeoxynucleotides. C A Stein, A M Krieg, eds. Applied Antisense Oligonucleotide Technology. John Wiley and Sons Inc., New York, N.Y. pp. 431-448.

Leung D Y M, Szefler S S. 1995. Steroid-Resistant Asthma. Med. Sci. Update 13(2), (http://library2.nationaljewish.orq/MSU/13n2MSU StRe Asthma.html).

Leung et al. 2002. Steroid-unresponsive asthma. Semin Respir Crit Care Med. 23(4):387-98.

Mannon P J, Fuss I J, Mayer L, Elson C O, Sandborn W J, Present D, Dolin B, Goodman N, Groden C, Hornung R L, Quezado M, Neurath M F, Salfeld J, Veldman G M, Schwertschlag U, Strober W. 2004. Anti-IL-12 Crohn's disease study group. Anti-interleukin-12 antibody for active Crohn's disease. N. Engl. J. Med. 351(20): 2069-2079.

Munkholm et al. 1994. Frequency of glucocorticoid resistance and dependency in Crohn's disease. Gut; 35(3):360-2.

Mariette X. 2003. Anti-cytokines in the treatment of inflammation. Rev. Prat. 53(5): 507-511.

Munck A, Guyre P M, Holbrook N.J. 1984. Physiological functions of glucocorticoids in stress and their relation to pharmacological actions. Endocr. Rev. 5(1): 25-44.

Neurath M F, Fuss I, Kelsall B L, Stuber E, Strober W. 1995. Antibodies to interleukin 12 abrogate established experimental colitis in mice. J. Exp. Med. 182(5): 1281-1290.

Re, F, Muzio, M, De Rossi, M, Polentarutti, N, Girl, J G., Mantovani, A, Colotta, F. 1994. The type II 'receptor' as a decoy target for interleukin 1 in polymorphonuclear leukocytes: characterization of induction by dexamethasone and ligand binding properties of the released decoy receptor. J. Exp. Med. 179: 739-743.

Ritter M, Buechler C, Langmann T, Orso E, Klucken J, Schmitz G. 1999. The scavenger receptor CD163: Regulation, promoter structure and genomic organization. Pathobiol. 67(5-6): 257-261.

Reinisch W and Vogelsang H. 2002. Steroid dependency in Crohn's disease. Gastroenterology, 123(1):393-5

Sambrook J, Russell D W. 2001. Molecular cloning. A laboratory manual. Cold Spring Harbor Laboratory Press, Cold Spring Harbor, N.Y.

Shadidi H, Vottero A, Stratakis C A, Taymans S E, Karl M, Longui C A, Chrousos G P, Daughaday W H, Gregory S A, Plate J M. 1999. Imbalanced expression of the glucocorticoid receptor isoforms in cultured lymphocytes from a patient with systemic glucocorticoid resistance and chronic lymphocytic leukemia. Biochem. Biophys. Res. Commun. 254(3): 559-565.

Sparwasser T, Koch E S, Vabulas R M, Heeg K, Lipford G B, Ellwart J W, Wagner H. 1998. Bacterial DNA and immunostimulatory CpG oligonucleotides trigger maturation and activation of murine dendritic cells. Eur. J. Immunol. 28(6): 2045-2054.

Stacey K J, Sweet M J, Hume D A. 1996. Macrophages ingest and are activated by bacterial DNA. J. Immunol. 157(5): 2116-2122.

Takeba Y, Nakafuchi H, Takeno m, Kashiwakura J, Suzuki N. 2002. Txk, a member of nonreceptor tyrosine kinase of Tec family, acts as a Th1 cell-specific transcription factor and regulates IFN-gamma gene transcription. J. Immunol. 168: 2365-2370.

Vermeer H, Hendriks-Stegeman B I, van Suylekom D, Rijkers G T, van Buul-Offers S C, Jansen M. 2004. An in vitro bioassay to determine individual sensitivity to glucocorticoids: induction of FKBP51 mRNA in peripheral blood mononuclear cells. Mol. Cell. Endocrinol. 218(1-2): 49-55.

Wolleben G, Erb K J. 2006. Immune stimulatory strategies for the prevention and treatment of asthma. Curr. Pharm. Des. 12(25): 3281-3292.

Wu W, Chaudhuri S, Brcikley D R, Pang D, Karrison T, Conzen S D. 2004. Microarray analysis reveals glucocorticoid-regulated survival genes that are associated with inhibition of apoptosis in breast epithelial cells. Cancer Res. 64(5): 1757-1764.

Zhao Q, Temsamani J, iadarola P L, Jiang Z, Agrawal S. 1996. Effect of different chemically modified oligodeoxynucleotides on immune stimulation. Biochem. Pharmacol. 51(2): 173-182.

Zimmerman S, Egeter O, Hausmann S, Lipford G B, Rocken M, Wagner H, Heeg K. 1998. CpG oligodeoxynucleotides trigger protective and curative Th1 responses in lethal murine Leishmaniasis. J. Immunol. 160(8): 3627-3630.

---

The invention claimed is:

1. An in vitro method for predicting if an immunomodulatory oligonucleotide can re-sensitize a patient suspected of being steroid resistant to the action of steroids, wherein the method comprises the steps of,
   isolating cells from a sample taken from said patient;
   cultivating said isolated cells in the presence of a steroid and an immunomodulatory oligonucleotide;
   determining an expression level of at least one marker gene from said cultivated cells, wherein said marker gene is a marker for re-sensitization to the action of steroids; and
   comparing said expression level of said at least one marker gene from said cultivated cells to an expression level of said at least one marker gene obtained from the cultivation of cells from healthy persons in the presence of said steroid and said immunomodulatory oligonucleotide or to a normalized expression level value of said expression level of said at least one marker gene obtained from the cultivation of cells from healthy persons in the presence of said steroid and said immunomodulatory oligonucleotide;
   wherein a similarity in the compared expression levels indicates that the immunomodulatory oligonucleotide is capable of re-sensitizing said patient to the action of steroids.

2. The method according to claim 1, wherein the at least one marker gene is selected from the group consisting of the genes CD163, Tsp1, and IL1-R2.

3. The method according to claim 1, wherein the at least one marker gene is selected from the group consisting of the genes CD163, Tsp1, IL1-R2, TLR2, TLR4, MKP-1 and TXK.

4. The method according to claim 1, wherein the at least one marker gene is CD163.

5. The method according to claim 1, wherein the cell is a blood cell.

6. The method according to claim 5, wherein the blood cell is a peripheral blood mononuclear cell (PBMC).

7. The method according to claim 1, wherein the patient exhibits symptoms of an inflammatory disease.

8. The method according to claim 7, wherein the inflammatory disease is selected from the group consisting of acute or chronic asthma, chronic obstructive pulmonary disease (COPD), ulcerative colitis, Crohn's disease, rheumatoid arthritis, psoriasis, and emphysema.

9. The method according to claim 1, further comprising selecting a therapy based on the compared expression levels.

10. The method according to claim 1, further comprising selecting a therapy employing said immunomodulatory oligonucleotide and a steroid when there is a similarity in the compared expression levels.

11. The method according to claim 1, further comprising the step of administering to the patient an immunomodulatory oligonucleotide and one or more of a steroid and an alternative therapeutic agent as a combination therapy.

12. The method according to claim 1, wherein the expression level of said marker gene is determined by nucleic acid amplification of said gene using gene specific primers, and quantifying the amplification results.

13. The method according to claim 1, wherein the expression level of said marker gene is determined by nucleic acid amplification of said gene using gene specific primers, and quantifying the amplification results and wherein the nucleic acid amplification is performed by a real time PCR using gene specific primers selected from SEQ ID NO: 1-14.

14. The method according to claim 1, wherein the expression level of said marker gene is determined by a protein expressed from said marker gene.

15. The method according to claim 14, wherein said expression level is determined by antibodies binding to said protein.

\* \* \* \* \*